United States Patent
Gerber

(10) Patent No.: US 7,904,149 B2
(45) Date of Patent: Mar. 8, 2011

(54) IMPLANTABLE MEDICAL ELONGATED MEMBER INCLUDING FIXATION ELEMENTS ALONG AN INTERIOR SURFACE

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 270 days.

(21) Appl. No.: 11/701,721

(22) Filed: Feb. 2, 2007

(65) Prior Publication Data

US 2008/0103534 A1 May 1, 2008

Related U.S. Application Data

(63) Continuation of application No. 11/591,279, filed on Oct. 31, 2006.

(51) Int. Cl.
*A61N 1/05* (2006.01)

(52) U.S. Cl. .............................. 607/2; 607/116

(58) Field of Classification Search .............. 607/2, 116, 607/117, 128
See application file for complete search history.

(56) References Cited

U.S. PATENT DOCUMENTS

| | | | |
|---|---|---|---|
| 4,033,357 A * | 7/1977 | Helland et al. ................ 607/121 |
| 4,402,328 A | 9/1983 | Doring | |
| 4,538,624 A | 9/1985 | Tarjan | |
| 4,590,949 A | 5/1986 | Pohndorf | |
| 4,658,835 A | 4/1987 | Pohndorf | |
| 4,716,888 A | 1/1988 | Wesner | |
| 4,796,643 A * | 1/1989 | Nakazawa et al. ............ 607/128 |
| 5,005,587 A | 4/1991 | Scott | |
| 5,300,107 A | 4/1994 | Stokes et al. | |
| 5,755,767 A | 5/1998 | Doan et al. | |
| 5,931,864 A * | 8/1999 | Chastain et al. .............. 607/128 |
| 5,991,668 A | 11/1999 | Leinders et al. | |
| 6,006,139 A | 12/1999 | Kruse et al. | |
| 6,188,932 B1 | 2/2001 | Lindegren | |
| 6,405,091 B1 | 6/2002 | Vachon et al. | |
| 6,510,347 B2 | 1/2003 | Borkan | |
| 6,587,733 B1 | 7/2003 | Cross, Jr. et al. | |
| 6,978,180 B2 * | 12/2005 | Tadlock ......................... 607/46 |
| 6,999,819 B2 | 2/2006 | Swoyer et al. | |
| 7,099,718 B1 * | 8/2006 | Thacker et al. ................ 607/117 |
| 7,460,913 B2 * | 12/2008 | Kuzma et al. .................. 607/116 |

(Continued)

FOREIGN PATENT DOCUMENTS

WO WO 2006/133445 A2 12/2006

OTHER PUBLICATIONS

Notification of Transmittal of the International Search Report and the Written Opinion of the International Searching Authority for patent application No. PCT/US2007/082819, mailed Jun. 18, 2008, 7 pages.

(Continued)

*Primary Examiner* — Michael Kahelin
(74) *Attorney, Agent, or Firm* — Shumaker & Sieffert, P.A.

(57) ABSTRACT

An implantable medical elongated member includes a first outer surface portion and a second outer surface portion extending around at least ten percent of an outer perimeter of the elongated member. A fixation element extends a distance from the first outer surface portion of the implantable medical elongated member. A longitudinally-extending section of the second outer surface portion proximate to a distal end of the elongated member is substantially devoid of any fixation elements that extend the distance from second outer surface portion.

25 Claims, 13 Drawing Sheets

U.S. PATENT DOCUMENTS

| | | | |
|---|---|---|---|
| 2002/0111661 | A1 | 8/2002 | Cross et al. |
| 2002/0156512 | A1 | 10/2002 | Borkan |
| 2003/0163184 | A1 | 8/2003 | Scheiner et al. |
| 2003/0199938 | A1 | 10/2003 | Smits et al. |
| 2003/0199962 | A1 | 10/2003 | Struble et al. |
| 2004/0210291 | A1 | 10/2004 | Erickson et al. |
| 2004/0230282 | A1 | 11/2004 | Cates et al. |
| 2005/0171587 | A1 | 8/2005 | Daglow et al. |
| 2005/0209653 | A1 | 9/2005 | Herbert et al. |
| 2006/0089690 | A1 | 4/2006 | Gerber |
| 2006/0235484 | A1* | 10/2006 | Jaax et al. ............... 607/46 |
| 2007/0100411 | A1 | 5/2007 | Bonde |
| 2007/0203556 | A1 | 8/2007 | Rutten et al. |
| 2007/0255370 | A1* | 11/2007 | Bonde et al. ............. 607/117 |

OTHER PUBLICATIONS

Reply to Written Opinion for corresponding patent application No. PCT/US2007/001957, filed Jun. 3, 2008, 17 pages.

Reply to Written Opinion for corresponding patent application No. PCT/US2007/082819, filed Sep. 15, 2008, 20 pages.

Notification of Transmittal of the International Search Report and the Written Opinion of the International Searching Authority for corresponding patent application No. PCT/US2007/001957, mailed Aug. 1, 2007, (12 pages).

Notification of Transmittal of the International Preliminary Report on Patentability for corresponding patent application No. PCT/US2007/082819, mailed Feb. 9, 2009, 11 pages.

Office Action for U.S. Appl. No. 11/591,279, dated Feb. 26, 2009, 10 pages.

Office Action for U.S. Appl. No. 11/706,146, dated Mar. 25, 2009, 16 pages.

Final Office Action for U.S. Appl. No. 11/591,279, dated Sep. 23, 2009, 14 pages.

Responsive Amendment for U.S. Appl. No. 11/591,279, filed Nov. 23, 2009, 24 pages.

Office Action for U.S. Appl. No. 11/591,279, dated Mar. 17, 2010, 10 pages.

Responsive Amendment for U.S. Appl. No. 11/591,279, filed Jun. 17, 2010, 9 pages.

* cited by examiner

IMPLANTABLE MEDICAL ELONGATED MEMBER INCLUDING FIXATION ELEMENTS ALONG AN INTERIOR SURFACE

This application is a continuation of application Ser. No. 11/591,279 (U.S. Publication No. US 2008/0103569), entitled, "IMPLANTABLE MEDICAL ELONGATED MEMBER INCLUDING FIXATION ELEMENTS ALONG AN INTERIOR SURFACE," and filed on Oct. 31, 2006, which is hereby incorporated by reference in its entirety.

TECHNICAL FIELD

The invention relates to medical device systems and, more particularly, to elongated members in medical device systems.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more implantable medical leads coupled to an electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form electrical signal s.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Thus, in order to deliver electrical stimulation to at least one of the S2, S3, or S4 sacral nerves, an implantable medical lead is implanted proximate to the sacral nerve(s).

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by implanting a lead proximate to the occipital nerve to deliver stimulation therapy.

In many electrical stimulation applications, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the implantable medical lead at the target stimulation site may minimize lead migration.

SUMMARY

In general, the invention is directed toward an implantable medical elongated member that includes one or more fixation elements along an interior surface of the elongated member, as well as a method for implanting the elongated member in a patient. The elongated member is configured to be coupled to a medical device to deliver a therapy from the medical device to target therapy delivery site in a patient. The therapy may be electrical stimulation, drug delivery, or both.

An "interior" surface of the elongated member is a portion of an outer surface of the elongated member that generally faces away from an epidermis layer of a patient (or a scalp of the patient, depending on the particular application of the elongated member) when implanted in subcutaneous tissue of the patient. Accordingly, an "exterior" side of the elongated member generally faces toward the epidermis of the patient when the elongated member is implanted in subcutaneous tissue of a patient. The elongated member may be implanted so that the fixation elements face inward away from an integumentary layer of the patient (e.g., the epidermis, dermis, or scalp), rather than outward so as to avoid damage to the integumentary layer or irritation to the patient from engagement of a fixation member with the integumentary layer. In one embodiment, the elongated member is fixed at one or more points that are distributed about less than a full outer perimeter of the elongated member in order to minimize or eliminate points of stress between the one or more fixation elements and the epidermis or scalp of a patient.

In accordance with one embodiment of the invention, at least a section of the exterior surface of the elongated member near a distal end of the elongated member is devoid of any fixation elements in order to help minimize or prevent stress points between the elongated member and an integumentary layer of the patient. In other embodiments, the exterior surface includes fixation elements that are sized to minimize any interference with the epidermis or scalp of the patient.

In one embodiment, the elongated member is an implantable medical lead that is coupled to an implantable or external electrical stimulator, which is configured to deliver electrical stimulation therapy to a target stimulation site in a patient via the lead, and more specifically, via at least one electrode disposed adjacent to a distal end of a lead body of the lead. The lead may be, for example, a cylindrical lead or a paddle lead. In another embodiment, the elongated member is a catheter configured to deliver a fluid, such as pharmaceutical agents, insulin, pain relieving agents, gene therapy agents, or the like from an implantable or external fluid reservoir and/or pump to a target tissue site in a patient.

The fixation element may be any suitable fixation element that helps substantially fix a position of the elongated member to (e.g., at or near) the target therapy delivery site, thereby reducing migration of the elongated member when the elongated member is implanted in a patient.

In one embodiment, the invention is directed to an apparatus comprising an implantable medical elongated member configured to couple to a medical device to deliver a therapy from the medical device to a target therapy delivery site in a patient. The elongated member extends between a proximal end and a distal end and defines an outer surface comprising a first outer surface portion, and a second outer surface portion extending around at least ten percent of an outer perimeter of the elongated member. The apparatus further comprises a fixation element extending a distance from the first outer surface portion of the implantable medical elongated member. A longitudinally-extending section of the second outer surface portion proximate to the distal end of the elongated member and extending around at least ten percent of the outer perimeter of the elongated member is substantially devoid of any fixation elements that extend the distance from second outer surface portion.

In another embodiment, the invention is directed to a system including a medical device and an elongated member. The implantable medical elongated member is configured to couple to the medical device to deliver a therapy from the medical device to a target therapy delivery site in a patient. The elongated member extends between a proximal end and a distal end and defines an outer surface comprising a first outer surface portion, and a second outer surface portion extending around at least ten percent of an outer perimeter of the elongated member. The apparatus further comprises a fixation element extending a distance from the first outer surface portion of the implantable medical elongated member. A longitudinally-extending section of the second outer surface portion proximate to the distal end of the elongated member and extending around at least ten percent of the outer perimeter of the elongated member is devoid of any fixation elements that extend the distance from second outer surface portion.

In yet another embodiment, the invention is directed toward an implantable medical lead comprising a lead body, one or more electrodes carried by the lead body, and one or more fixation elements extending from an outer surface of the lead body. At least a circumferential sub-section of the outer surface extending over at least ten degrees is substantially devoid of the fixation elements.

In yet another embodiment, the invention is directed to method for implanting an elongated member in a patient. The method comprises introducing the elongated member a patient. The elongated member extends between a proximal end and a distal end and defines an outer surface comprising a first outer surface portion and a second outer surface portion extending around at least ten percent of an outer perimeter of the elongated member. The elongated member further comprises a fixation element extending a distance from the first outer surface portion of the implantable medical elongated member. A longitudinally-extending section of the second outer surface portion proximate to the distal end of the elongated member and extending around at least ten percent of the outer perimeter of the elongated member is substantially devoid of any fixation elements that extend the distance from second outer surface portion. The method further comprises orienting the elongated member so that the second outer surface portion faces a superficial direction and advancing the elongated member through the introducer to a target therapy delivery site to deploy the fixation member into tissue of the patient, wherein the fixation element engages with surrounding tissue to substantially fix a position of the elongated member proximate to the target therapy delivery site.

The details of one or more embodiments of the invention are set forth in the accompanying drawings and the description below. Other features, objects, and advantages of the invention will be apparent from the description and drawings, and from the claims.

DETAILED DESCRIPTION

The present invention relates to an implantable medical elongated member including one or more fixation elements disposed about an outer surface of the elongated member in an arrangement that minimizes or eliminates points of stress between the fixation elements and an integumentary layer (e.g., an epidermis layer, dermis or scalp) of a patient. For example, the elongated member may include fixation elements that radially extend from less than a full outer circumference of a lead body or fixation elements disposed along one outer surface portion of the elongated member. Due to the arrangement of the fixation elements about the outer surface of the elongated member, the elongated member may be implanted so that the fixation elements do not interfere with the epidermis, dermis, or scalp of the patient. For example, the elongated member may be implanted such that the fixation elements may face away from the epidermis, dermis, or scalp of the patient.

The elongated member is configured to be coupled to a medical device to deliver a therapy from the medical device to target tissue in a patient. Various embodiments of the elongated member may be applicable to different therapeutic applications. For example, the elongated member may be a stimulation lead or a lead extension that is used to deliver electrical stimulation to a target stimulation site and/or sense parameters (e.g., blood pressure, temperature or electrical activity) of a patient. In another embodiment, the elongated member may be a catheter that is placed to deliver a fluid, such as pharmaceutical agents, insulin, pain relieving agents, gene therapy agents or the like from a fluid delivery device (e.g., a fluid reservoir and/or pump) to a target tissue site in a patient. The invention is applicable to any configuration or type of implantable elongated member that is used to deliver therapy to a site in a patient. For purposes of illustration, however, the disclosure will refer to a neurostimulation lead.

Figure 1:
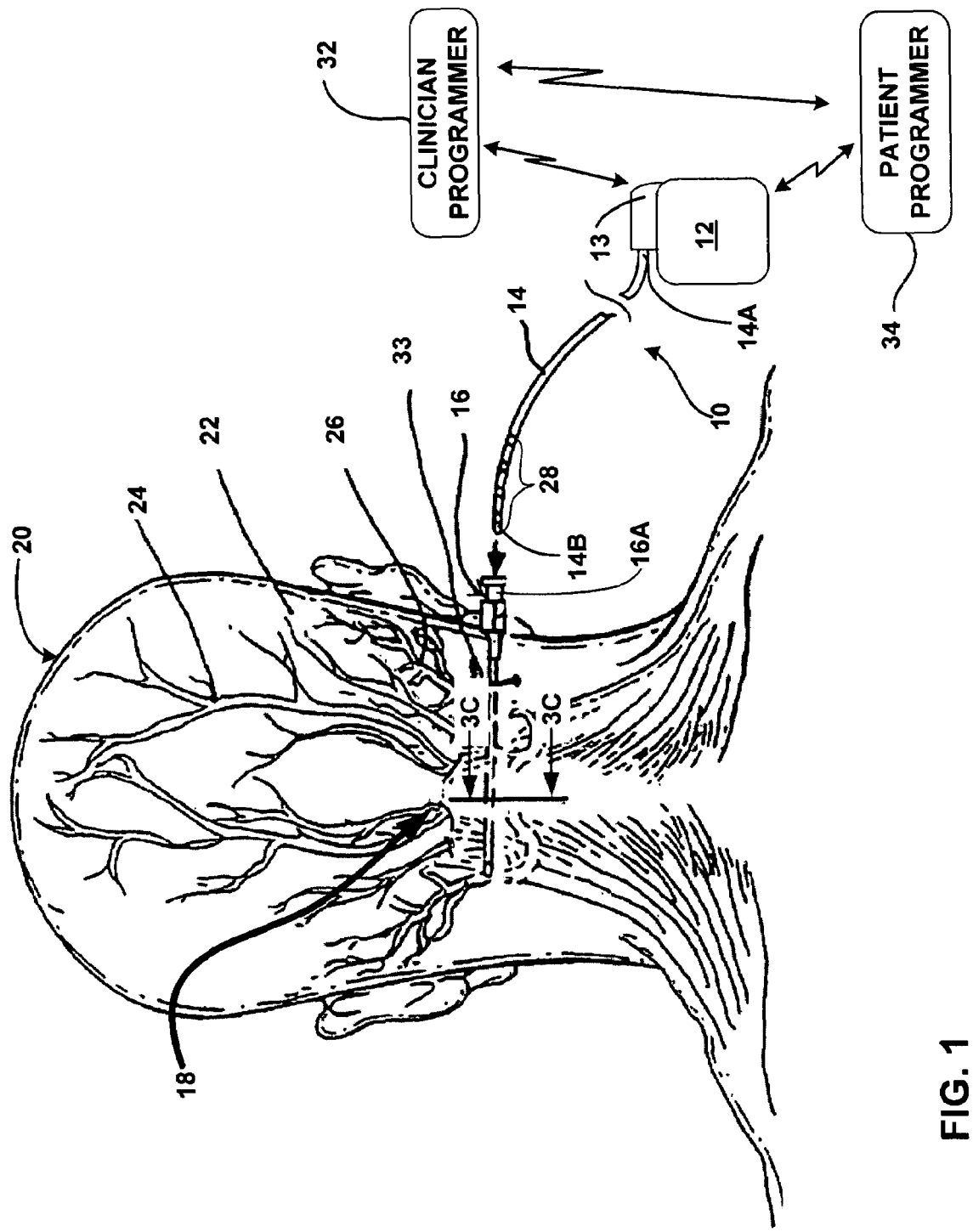
FIG. 1 illustrates the implantation of a therapy system, which includes an electrical stimulator coupled to an implantable medical lead, at a location proximate to an occipital nerve.

FIG. 1 a schematic perspective view of a therapy system 10, which includes an electrical stimulator 12 coupled to implantable medical lead 14. Lead 14 is aligned to be introduced into introducer needle 16, which is positioned proximate to target stimulation site 18 of patient 20. In particular, lead 14 is aligned to be implanted and anchored or fixated with fixation elements proximate to target stimulation site 18 within patient 20 for stimulation of one or more occipital nerves. In the example shown in FIG. 1, target stimulation site 18 is proximate to at least one of lesser occipital nerve 22, greater occipital nerve 24 or third occipital nerve 26. In alternate embodiments, lead 14 may be positioned proximate to one or more other peripheral nerves proximate to occipital nerves 22, 24, and 26 of patient 20, such as nerves branching from occipital nerves 22, 24 or 26. In addition, therapy system 10 may be used to provide stimulation therapy to any other suitable nerves within patient 20, such as, but not limited to, trigeminal nerves, branches of trigeminal nerves or nerves within a brain, stomach or spinal cord of patient 20.

In the embodiment shown in FIG. 1, electrical stimulator 12 is a neurostimulator that is either implantable or external. For example, neurostimulator 12 may be subcutaneously implanted in the body of a patient (e.g., in a chest cavity, lower back, lower abdomen, or buttocks of patient 20). Neurostimulator 12 provides a programmable stimulation signal (e.g., in the form of electrical pulses or substantially continuous-time signals) that is delivered to target stimulation site 18 by implantable medical lead 14, and more particularly, via one or more stimulation electrodes 28 carried by lead 14. In some embodiments, neurostimulator 12 may be coupled to two or more leads, e.g., for bilateral or multi-lateral stimulation. Stimulation of occipital nerves 22, 24, and 26 may help alleviate pain associated with, for example, chronic migraines, cervicogenic headaches, occipital neuralgia or trigeminal neuralgia. Neurostimulator 12 may also be referred to as a pulse generator. In some embodiments, lead 14 may also carry one or more sense electrodes to permit neurostimulator 12 to sense electrical signals from target stimulation site 18.

Proximal end 14A of lead 14 may be both electrically and mechanically coupled to connector 13 of neurostimulator 12 either directly or indirectly (e.g., via a lead extension). In particular, conductors disposed within a lead body of lead 14 electrically connect stimulation electrodes 28 (and sense electrodes, if present) located adjacent to distal end 14B of lead 14 to neurostimulator 12.

As described in further detail below, lead 14 further includes one or more one fixation elements (not shown in FIG. 1) extending from an interior portion of an outer surface of lead 14 to help substantially fix lead 14 proximate to target stimulation site 18. In the embodiment shown in FIG. 1, an interior portion of the outer surface of lead 14 faces away from scalp 30 of patient 20. By including one or more fixation elements that face away from scalp 30, and including substantially no fixation elements on a side facing scalp 30, the possibility of a fixation element (which may protrude from lead 14) extending into or through scalp 30 is minimized or eliminated. At the same time, however, the inward-facing fixation elements are effective in resisting displacement of lead 14, and particularly electrodes 28, from the stimulation site. In one embodiment, an exterior portion of the outer surface of lead (i.e., a portion that faces scalp 30 when lead 14 is implanted in patient 20) is devoid of any fixation elements, which may contribute to the comfort of patient 20 and avoidance of tissue erosion or damage when lead 14 is implanted in patient 20.

In the application of therapy system 10 shown in FIG. 1, implantation of lead 14 may involve the subcutaneous placement of lead 14 transversely across one or more occipital nerves 22, 24, and/or 26 that are causing patient 20 to experience pain. Where treating occipital neuralgia, patient 30 may be placed in a lateral position or in a prone position during implantation of lead 14.

In order to locate the specific occipital nerve causing pain, a clinician may palpate the area of pain. In addition, some embodiments, a screening lead may be used prior to implanting lead 14 to develop optimal stimulation parameters (e.g., various electrode combinations, amplitude, pulse width or rate).

In one example method of implanting lead 14 proximate to one or more occipital nerves 22, 24, and/or 26, a vertical skin incision 33 approximately two centimeters in length is made in the neck of patient 20 lateral to the midline of the spine at the level of the C1 vertebra. Fluoroscopy may be used to identify the location of the C1 vertebra. Typically, local anesthetic is used during the implantation procedure. The length of vertical skin incision 33 may vary depending on the particular patient. At this location, the patient's skin and muscle are separated by a band of connective tissue referred to as fascia. Introducer needle 16, which may be a Tuohy needle, is introduced into the subcutaneous tissue, superficial to the fascia and muscle layer but below the skin. In some embodiments, introducer needle 16 may be manually curved by the clinician to conform to the contour of the body of patient 20 proximate to the peripheral nerve, and in the embodiment shown in FIG. 1, the clinician may conform introducer needle 16 to the contour of the neck of patient 20.

Occipital nerves 22, 24, and 26 are located within the cervical musculature and overlying fascia, and as a result, introducer needle 16, and eventually lead 14, are inserted superior to occipital nerves 22, 24, and 26. That is, in one embodiment, introducer needle 16 is introduced into the fascia layer of patient 20 such that introducer needle 16 is between the skin of patient 20 and the occipital nerve 22, 24, and/or 26 to be stimulated.

Introducer needle 16 may be guided transversely from incision 33 across the midline of the spine of patient 16. Fluoroscopic observation may aid the clinician in identifying the trunk of the occipital nerve.

Once introducer needle 16 is fully inserted, a needle stylet may be removed from the introducer needle, if introducer needle 16 includes a stylet. Lead 14 may then be advanced through introducer needle 16 and positioned to allow stimulation of the lesser occipital nerve 22, greater occipital nerve 24, third occipital nerve 26, and/or other peripheral nerves proximate to an occipital nerve. The position of lead 14 may be verified via fluoroscopy or another suitable technique. In addition, the clinician may confirm that the electrodes proximate to distal end 14A of lead 14 are properly placed with respect to the particular occipital nerve. For example, the clinician may provide electrical signals to the electrodes and patient 30 may provide feedback relating to the paresthesia coverage. Upon placement of lead 14, introducer needle 16 may be removed (either before or after confirming the placement of the electrodes). As described below, in one embodiment, upon removal of introducer needle 16, the one or more fixation elements of lead 14 engage with surrounding tissue to substantially fix a position of lead 14 proximate to target stimulation site 18. In another embodiment, the one or more fixation elements of lead 14 adhere to surrounding tissue to substantially fix a position of lead 14.

Accurate lead placement may affect the success of occipital nerve stimulation, as well as any other nerve stimulation application of therapy system 10. If lead 14 is located too deep, i.e. anterior, in the subcutaneous tissue, patient 20 may experience muscle contractions, grabbing sensations, or burning. Such problems may additionally occur if lead 14 migrates after implantation. Furthermore, due to the location of implanted lead 14 on the back of the neck of patient 20, lead 14 may be subjected to pulling and stretching that may increase the chances of lead migration. For these reasons, fixating lead 14 may be advantageous.

Although occipital nerve stimulation is shown in FIG. 1, therapy system 10 is useful in other neurostimulation applications. In alternate applications of lead 14, target stimulation site 18 may be a location proximate to other nerves, organs, muscles, muscle groups or other tissue sites in patient 20, which may be selected based on, for example, a therapy program selected for a particular patient 20. For example, therapy system 10 may be used to deliver neurostimulation therapy to a sacral nerve, a pudendal nerve, a perineal nerve or other areas of the nervous system, in which cases, lead 14 would be implanted and substantially fixed proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 20 and target stimulation site 18 of FIG. 1 are referenced throughout the remainder of the disclosure for purposes of illustration, a neurostimulation lead 14 in accordance with the invention may be adapted for use in a variety of electrical stimulation applications.

Therapy system 10 may also include clinician programmer 32 and patient programmer 34. Clinician programmer 32 may be a handheld computing device that permits a clinician to program neurostimulation therapy for patient 20, e.g., using input keys and a display. For example, using clinician programmer 32, the clinician may specify neurostimulation parameters for use in delivery of neurostimulation therapy. Clinician programmer 32 supports telemetry (e.g., radio frequency (RF) telemetry) with neurostimulator 12 to download neurostimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 32, patient programmer 34 may be a handheld computing device. Patient programmer 34 may also include a display and input keys to allow patient 20 to interact with patient programmer 34 and neurostimulator 12. In this manner, patient programmer 34 provides patient 20 with an interface for control of neurostimulation therapy by neurostimulator 12. For example, patient 20 may use patient programmer 34 to start, stop or adjust neurostimulation therapy. In particular, patient programmer 34 may permit patient 20 to adjust stimulation parameters such as duration, amplitude, pulse width and pulse rate, within an adjustment range specified by the clinician via clinician programmer 34, or select from a library of stored stimulation therapy programs.

Neurostimulator 12, clinician programmer 32, and patient programmer 34 may communicate via cables or a wireless communication, as shown in FIG. 1. Clinician programmer 32 and patient programmer 34 may, for example, communicate via wireless communication with neurostimulator 12 using RF telemetry techniques known in the art. Clinician programmer 32 and patient programmer 34 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 2:
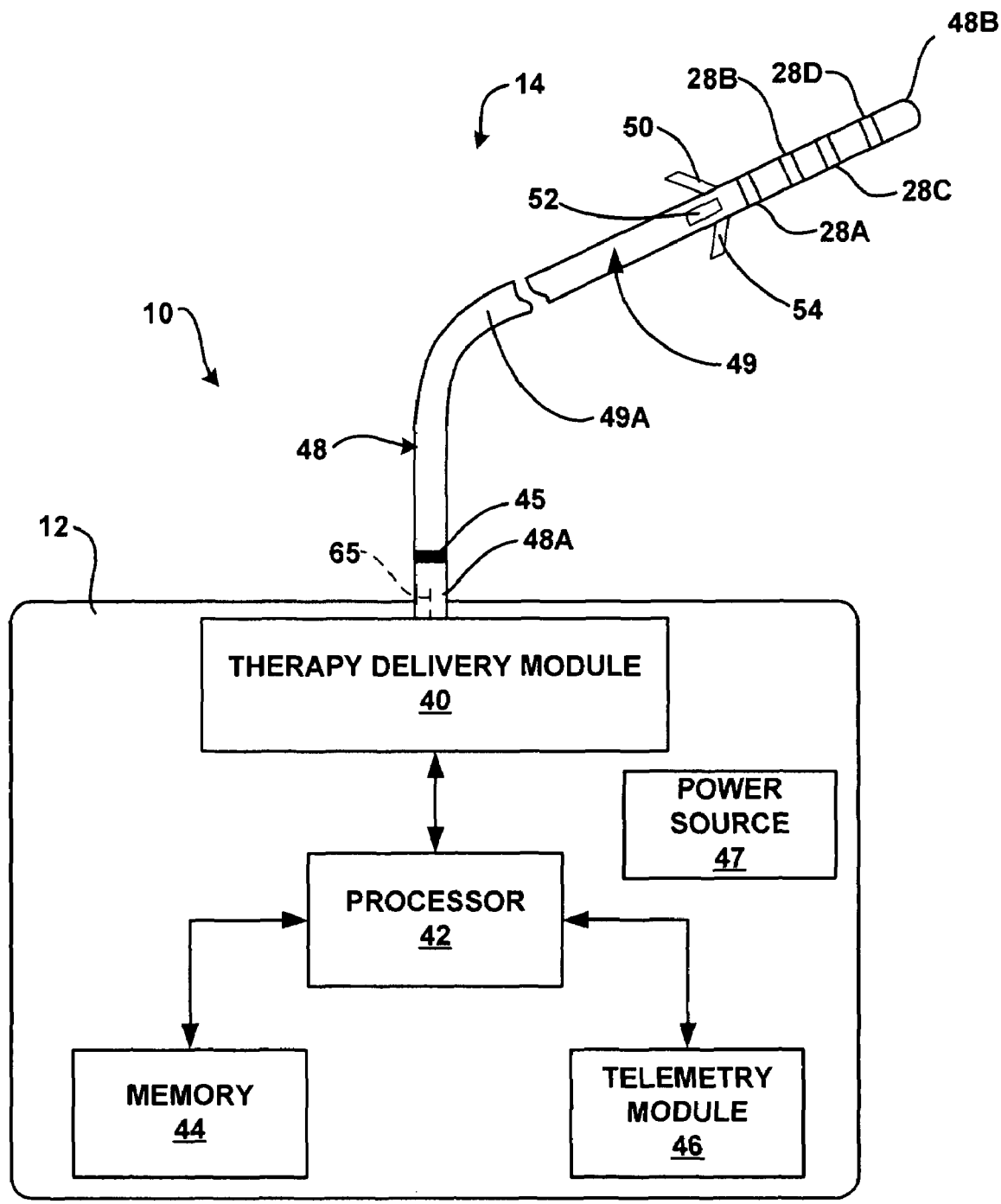
FIG. 2 is a block diagram illustrating various components of the electrical stimulator and implantable lead of the therapy system of FIG. 1.
Figure 11:
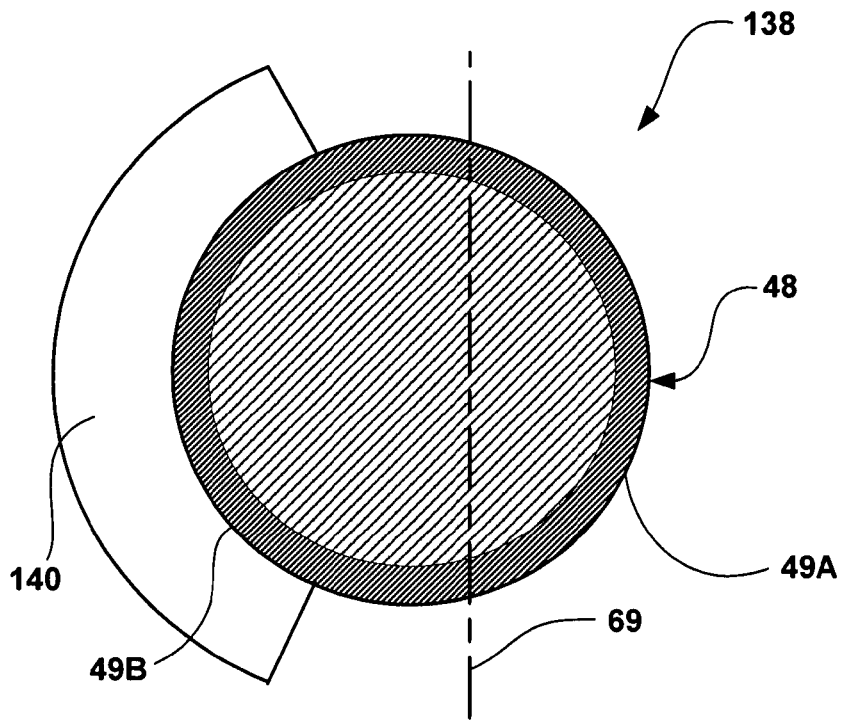
FIG. 11 is a schematic cross-sectional view of a lead including a fixation element extending around less than a full first outer surface portion of a lead body.

FIG. 2 is a block diagram illustrating various components of neurostimulator 12 and an implantable medical lead 14. Neurostimulator 12 includes therapy delivery module 40, processor 42, memory 44, telemetry module 46, and power source 47. In some embodiments, neurostimulator 12 may also include a sensing circuit (not shown in FIG. 2). Implantable medical lead 14 includes lead body 48 extending between proximal end 48A and distal end 48B. In the embodiment of FIG. 2, lead body 48 is cylindrical and defines an outer surface including a first portion 49A, which is facing away from the plane of the image of FIG. 2. The outer surface of lead body 48 further defines a second portion 49B (not shown in FIG. 2) that faces into the plane of the image of FIG. 2. In other embodiments, lead body 48 may be paddle-shaped (i.e., a "paddle" lead), in which case lead body 48 would define two opposing surfaces, as shown in FIG. 11 with respect to lead 142.

Electrodes 28A, 28B, 28C, and 28D (collectively "electrodes 28") are disposed on lead body 48 adjacent to distal end 48B of lead body 48. In some embodiments, electrodes 28 may be ring electrodes. In other embodiments, electrodes 28 may be segmented or partial ring electrodes, each of which extends along an arc less than 360 degrees (e.g., 90-120 degrees) around the circumference of lead body 48. The configuration, type, and number of electrodes 28 illustrated in FIG. 2 are merely exemplary.

In embodiments in which lead 14 is a paddle lead, electrodes 28 may extend along one side of lead body 48. Electrodes 28 extending around a portion of the circumference of lead body 48 or along one side of a paddle lead may be useful for providing an electrical stimulation field in a particular direction/targeting a particular therapy deliver site. For example, in the electrical stimulation application shown in FIG. 1, electrodes 28 may be disposed along lead body 48 such that the electrodes face toward occipital nerves 22, 24, and/or 26, or otherwise away from scalp 30. This may be an efficient use of stimulation because electrical stimulation of scalp 30 may not provide any or very minimal useful therapy to patient 20. In addition, the use of segmented or partial ring electrodes 28 may also reduce the overall power delivered to electrodes 28 by neurostimulator 12 because of the efficient delivery of stimulation to occipital nerves 22, 24, and/or 26 (or other target stimulation site) by eliminating or minimizing the delivery of stimulation to unwanted or unnecessary regions within patient 20.

In embodiments in which electrodes 28 extend around a portion of the circumference of lead body 48 or along one side of a paddle lead, lead 14 may include one or more orientation markers 45 proximate to proximal end 14A that indicate the relative location of electrodes 28. Orientation marker 45 may be a printed marking on lead body 48, an indentation in lead body 48, a radiographic marker, or another type of marker that is visible or otherwise detectable (e.g., detectable by a radiographic device) by a clinician. Orientation marker 45 may help a clinician properly orient lead 14 such that electrodes 28 face the desired direction (e.g., toward occipital nerves 22, 24, and/or 26) within patient 20. For example, orientation marker 45 may also extend around the same portion of the circumference of lead body 48 or along the side of the paddle lead as electrodes 28. In this way, orientation marker 45 faces the same direction as electrodes, thus indicating the orientation of electrodes 28 to the clinician. When the clinician implants lead 14 in patient 20, orientation marker 45 may remain visible to the clinician.

Neurostimulator 12 delivers stimulation therapy via electrodes 28 of lead 14. In particular, electrodes 28 are electrically coupled to a therapy delivery module 40 of neurostimulator 12 via conductors within lead body 48. In one embodiment, an implantable signal generator or other stimulation circuitry within therapy delivery module 40 delivers electrical signals (e.g., pulses or substantially continuous-time signals, such as sinusoidal signals) to targets stimulation site 18 (FIG. 1A) via at least some of electrodes 28 under the control of a processor 42. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The signal s may be delivered from therapy delivery module 40 to electrodes 28 via a switch matrix and conductors carried by lead 14 and electrically coupled to respective electrodes 28.

Processor 42 may include a microprocessor, a controller, a DSP, an ASIC, an FPGA, discrete logic circuitry, or the like. Processor 42 controls the implantable signal generator within therapy delivery module 40 to deliver neurostimulation therapy according to selected stimulation parameters. Specifically, processor 42 controls therapy delivery module 40 to deliver electrical signal s with selected amplitudes, pulse widths (if applicable), and rates specified by the programs. In addition, processor 42 may also control therapy delivery module 40 to deliver the neurostimulation signals via selected subsets of electrodes 28 with selected polarities. For example, electrodes 28 may be combined in various bipolar or multipolar combinations to deliver stimulation energy to selected sites, such as nerve sites adjacent the spinal column, pelvic floor nerve sites, or cranial nerve sites.

Processor 42 may also control therapy delivery module 40 to deliver each stimulation signal according to a different program, thereby interleaving programs to simultaneously treat different symptoms or provide a combined therapeutic effect. For example, in addition to treatment of one symptom such as sexual dysfunction, neurostimulator 12 may be configured to deliver neurostimulation therapy to treat other symptoms such as pain or incontinence.

Memory 44 of neurostimulator 12 may include any volatile or non-volatile media, such as a RAM, ROM, NVRAM, EEPROM, flash memory, and the like. In some embodiments, memory 44 of neurostimulator 12 may store multiple sets of stimulation parameters that are available to be selected by patient 20 via patient programmer 34 (FIG. 1) or a clinician via clinician programmer 32 (FIG. 1) for delivery of neurostimulation therapy. For example, memory 44 may store stimulation parameters transmitted by clinician programmer 32 (FIG. 1). Memory 44 also stores program instructions that, when executed by processor 42, cause neurostimulator 12 to deliver neurostimulation therapy. Accordingly, computer-readable media storing instructions may be provided to cause processor 42 to provide functionality as described herein.

In particular, processor 42 controls telemetry module 46 to exchange information with an external programmer, such as clinician programmer 32 and/or patient programmer 34 (FIG. 1), by wireless telemetry. In addition, in some embodiments, telemetry module 46 supports wireless communication with one or more wireless sensors that sense physiological signals and transmit the signals to neurostimulator 12.

As previously discussed, migration of lead 14 following implantation may be undesirable, and may have detrimental effects on the quality of therapy delivered to a patient 20. For example, with respect to the occipital nerve stimulation application shown in FIG. 1, migration of lead 14 may cause displacement of electrodes 28 carried adjacent to distal end 14B of lead 14 with respect to target stimulation site 18. In such a situation, the electrodes may not be properly positioned to deliver therapy to target stimulation site 18, resulting in reduced electrical coupling, and possibly undermining therapeutic efficacy of the neurostimulation therapy from system 10.

Substantially fixing lead 14 to surrounding tissue may help prevent lead 14 from migrating from target stimulation site 18 following implantation, which may ultimately help avoid harmful effects that may result from a migrating lead 14. However, while it may be desirable to fix lead 14 such that electrodes 28 remain proximate to target stimulation site 18 (FIG. 1), in some situations, it may also be desirable to minimize discomfort to patient 20 from lead 14. For example, when lead 14 is implanted in a dermis or subcutaneous tissue of patient 20 (FIG. 1), such as in the occipital nerve stimulation application shown in FIG. 1, patient 20 may be more aware of lead 14 due to the location of lead 14 near an epidermis, scalp 30 or another integumentary layer of patient 20.

To that end, lead 14 includes fixation elements 50, 52, and 54 (not shown in FIG. 3A) along a first portion 49A of outer surface 49 of lead body 48 to minimize migration of lead 14 and substantially fix a position of electrodes 28 proximate to target stimulation site 18. When lead 14 is implanted proximate to target stimulation site 18, lead body 48 may be oriented such that first portion 49A ("first outer surface portion") of outer surface 49 generally faces away from the scalp 30 of patient and in an inward, deep direction and a majority of second portion 49B ("second outer surface portion") (shown in FIG. 3B) faces outward in a superficial direction. In this way, first portion 49A of outer surface 49 may also be referred to as an "interior surface" of lead body 48 and second portion 49B may also be referred to as an "exterior surface" of lead body 48. During implantation, the caregiver will take note of the interior and exterior surfaces 49A, 49B of lead body 48 and appropriately position lead 14 so that the interior and exterior surfaces face inward and outward, respectively.

Fixation elements 50, 52, and 54 engage with surrounding tissue at target stimulation site 18 to fix a position of lead 14. When lead 14 is implanted in patient 20 such that first outer surface portion 49A of lead body 48 faces away from scalp 30

(or another integumentary layer) of patient 20, fixation elements 50 and 54 extend substantially parallel to scalp 30 and fixation element 52 extends away from scalp 30. In the embodiment of lead 14 shown in FIG. 2, second portion 49B of outer surface 49 of lead body 48 is devoid of any fixation elements. As a result, lead 14 does not include any fixation elements that may extend into scalp 30, and possibly protrude through scalp 30, thereby resulting in an implantable medical lead 14 that is more comfortable to patient 20 and reduces the possibility of erosion or damage to subcutaneous tissue.

Although lead 14 includes three fixation elements 50, 52, and 54 in the embodiment shown in FIG. 2, lead 14 may include any suitable number of fixation elements 50, 52, and 54. Furthermore, fixation elements 50, 52, and 54 need not be protrusions that extend from lead 14. Fixation elements 50, 52, and 54 may be any suitable actively or passively deployed fixation element that helps prevent migration of lead 14 when lead 14 is implanted in patient 20, such as, but not limited to, one or more tines, barbs, hooks, wire-like elements, adhesives (e.g., surgical adhesives), balloon-like fixation elements, pinning fixation elements, collapsible or expandable fixation structures, and so forth. Fixation elements 50, 52, and 54 may be composed of any suitable biocompatible material, including, but not limited to, polymers, titanium, stainless steel, Nitinol, other shape memory materials, hydrogel or combinations thereof.

Fixation elements 50, 52, and 54 may be any suitable size, which may depend on the particular application of lead 14. In particular, it may be desirable to select the size of or otherwise configure fixation elements 50, 52, and 54 to fix lead 14 to a particular region of the patient proximate to the target stimulation site (e.g., a peripheral nerve stimulation site), which may involve selecting the size of fixation elements 50, 52, and 54 to accommodate the specific anatomical configuration of a region of the patient proximate to the peripheral nerve.

Furthermore, fixation elements 50, 54, and 54 may not be attached directly to lead 14, but may be carried by another apparatus that is attached to the elongated member, such as a sleeve or mounting band. An example of a mounting band is described in commonly-assigned U.S. Pat. No. 6,999,819, entitled "IMPLANTABLE MEDICAL ELECTRICAL STIMULATION LEAD FIXATION METHOD AND APPARATUS" and issued on Feb. 14, 2006, which is hereby incorporated by reference in its entirety.

Examples of suitable hydrogel fixation elements are described in commonly assigned U.S. Patent Application Publication No. 2006/0095077, entitled "EXPANDABLE FIXATION STRUCTURES and filed on Oct. 29, 2004, U.S. Patent Application Publication No. 2006/0095078, entitled "EXPANDABLE FIXATION MECHANISM" and filed on Oct. 29, 2004, and U.S. patent application Ser. No. 11/591,174 by Martin T. Gerber, entitled "IMPLANTABLE MEDICAL ELONGATED MEMBER INCLUDING EXPANDABLE FIXATION MEMBER" and filed on the same date as the present disclosure.

Other suitable fixation elements may include wire-like fixation elements as described in commonly assigned U.S. Patent Application Publication No. 2005/0096718, entitled "IMPLANTABLE STIMULATION LEAD WITH FIXATION MECHANISM" and filed on Oct. 31, 2003 and commonly-assigned U.S. patent application Ser. No. 11/591,282 by Martin T. Gerber, entitled "IMPLANTABLE STIMULATION LEAD INCLUDING WIRE-LIKE FIXATION ELEMENTS" and filed on the same date as the present disclosure. An example of tine fixation elements is described in U.S. Pat. No. 6,999,819, entitled "IMPLANTABLE MEDICAL ELECTRICAL STIMULATION LEAD FIXATION METHOD AND APPARATUS" and filed on Nov. 9, 2001.

An example of a suitable lead including a tissue-receiving cavity is described in commonly-assigned U.S. patent application Ser. No. 11/591,294 by Martin T. Gerber, entitled "IMPLANTABLE MEDICAL ELONGATED MEMBER INCLUDING A TISSUE RECEIVING CAVITY" and filed on the same date as the present disclosure. An example of a suitable in situ formed fixation element is described in commonly-assigned U.S. patent application Ser. No. 11/591,433 by Martin T. Gerber, entitled "IMPLANTABLE MEDICAL ELONGATED MEMBER WITH IN SITU FORMED FIXATION ELEMENT" and filed on the same date as the present disclosure. An example of suitable balloon-like fixation elements are described in commonly-assigned U.S. patent application Ser. No. 11/591,447 by Martin T. Gerber, entitled, "IMPLANTABLE STIMULATION LEAD INCLUDING BALLOON FIXATION ELEMENT" and filed on the same date as the present disclosure.

Each of the aforementioned patents and patent applications relating to suitable fixation elements are herein incorporated by reference in their entirety.

Figure 3A:
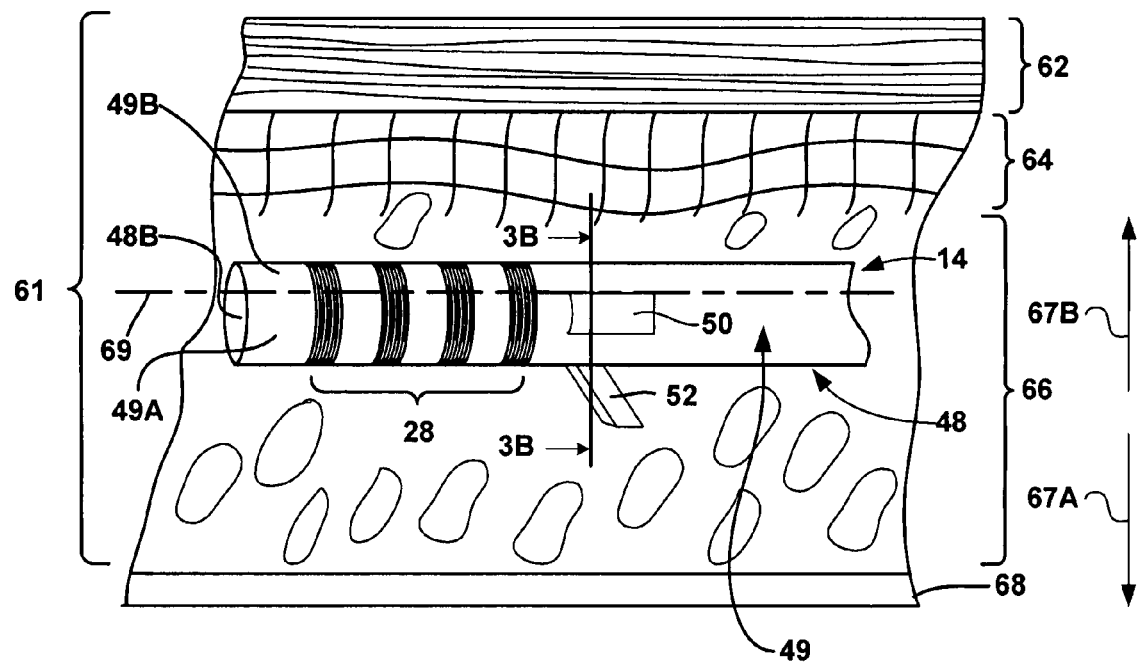
FIG. 3A is a perspective view of the implantable medical lead of FIG. 1 implanted in subcutaneous tissue.
Figure 3B:
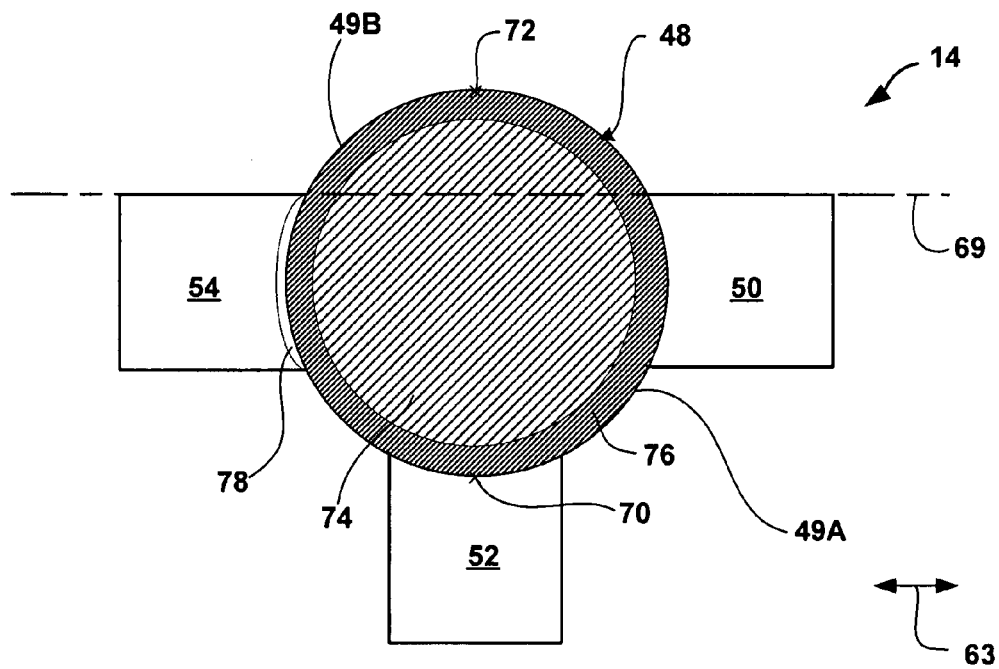
FIG. 3B is a schematic cross-sectional view of the implantable medical lead of FIGS. 1-3A.

FIG. 3A illustrates a schematic cross-sectional view of skin 61 of patient 20, which includes epidermis 62, dermis 64, and subcutaneous tissue 66, as well as a portion of a nerve 68. FIG. 3A further shows a perspective view of implantable medical lead 14 of FIGS. 1 and 2 implanted in a subcutaneous tissue 66 proximate to nerve 68. FIG. 3B illustrates a schematic cross-sectional view of lead 14 taken along line 3B-3B in FIG. 3A.

Distal end 48B of lead body 48 is shown in FIG. 3A. Proximal end 48A of lead body 48, which contains contacts (not shown in FIGS. 3A and 3B) to electrically couple lead 14 (and in particular, electrodes 28) to a lead extension or a neurostimulator (e.g., neurostimulator 12 in FIG. 1). Skin 61 and nerve 68 are general representations of a region of patient 20 and are shown to aid in the description of the invention, and thus, are not necessarily specific to a specific nerve of patient 20, nor drawn to any particular scale.

If neurostimulator 12 (FIGS. 1 and 2) is implanted in patient 20, the entire length of lead 14 is typically implanted in patient 20. On the other hand, if neurostimulator 12 is external, lead 14 may be partially implanted within patient 20 and lead 14 (or a lead extension to which proximal end 14A (shown in FIG. 1) is coupled) may extend through epidermis layer 62 via a percutaneous port.

As previously discussed, lead body 48 defines outer surface 49, which includes first ("interior") outer surface portion 49A and second ("exterior") outer surface portion 49B, which are demarcated by line 69 in FIG. 3A. In general, first outer surface portion 49A and second outer surface portion 49B do not overlap and have center points 70 and 72 that are generally opposite each other. Center points 70 and 72 are shown in FIG. 3B and referred to herein as reference points to aid in the description of the invention. Fixation elements 50, 52, and 54 (shown in FIG. 3B) are distributed about less than a full outer perimeter of lead body 48 because first outer surface portion 49A extends around less than a full outer perimeter of lead body 48. The outer perimeter of lead body 48 is the outer circumference of lead body 48. In embodiments in which a lead includes a noncircular cross-section, the outer perimeter of the lead body is defined by the outermost edge of a cross-section of the lead body.

In the embodiment shown in FIG. 3A, first outer surface portion 49A has a larger size (i.e. measured in terms of surface area) than second outer surface portion 49B. In particular, in the embodiment shown in FIGS. 3A-B, second outer surface portion 49B extends around less than or equal to about 50 percent (%) of the outer perimeter of lead body 48. In one embodiment, second outer surface portion 49B extends around at least 10% of the outer perimeter of lead body 48, while second outer surface portion 49A extends around about 50% to about 90% of the outer perimeter of lead body 48. In the embodiment shown in FIGS. 3A-B, first outer surface portion 49A extends around approximately 75% of the outer perimeter of lead body 48. Therefore, fixation elements 50, 52, and 54 are distributed about approximately 75% of the outer perimeter of lead body 48. In some embodiments, first and second portions 49A and 49B may be the same size. For example, demarcation line 69 may extend through a center of lead body 48, such that first and second outer surface portions 49A and 49B each define a half of lead body 48. Alternatively, demarcation line 69 may be moved toward center point 70 of first portion 49A to define a second portion 49B that is a greater (i.e., has a greater surface area) than first portion 49A.

In embodiments in which lead body 48 has a circular cross-section, the percentages given above can be translated to a percentage of a circle. For example, in the embodiment shown in FIGS. 3A-B, first outer surface portion 49A extends around approximately 75% of the outer perimeter of lead body 48, or alternatively, extends over about 270°.

Regardless of the respective sizes of first and second outer surface portions 49A and 49B, lead 14 may be oriented and implanted in patient such that first outer surface portion 49A (particularly center point 70) generally faces a deep direction 67A (i.e., faces away from epidermis 62), while a majority of second outer surface portion 49B (particularly center point 72) faces a superficial direction 67B (i.e., faces toward epidermis 62). Of course, due to the cylindrical shape of lead body 48 in the example of FIGS. 3A and 3B, at least some of first outer surface portion 49A neither faces toward nor away from epidermis 62, but rather faces a direction 63 (shown in FIG. 3B) that is generally parallel to epidermis 62. Only a small percentage of second outer surface portion 49B faces direction 63, and thus, it can be said that the "majority" of second outer surface portion 49B faces a superficial direction.

Lead 14 may include a visible marker 65 (shown in FIG. 2 in phantom) on the proximal end 48A of lead body 48. Visible marker 65 may provide a reference point for a clinician during implantation of lead 14 in patient 20. For example, the clinician may use visible marker 65 to orient lead 14 such that first outer surface portion 49A faces a deep direction when lead 14 is implanted in patient 20. Visible marker 65 may be a printed marking on lead body 48, an indentation in lead body 48, a radiographic marker, or another type of marker that is visible or otherwise detectable (e.g., detectable by a radiographic device) by a clinician. In FIG. 2, visible marker 65 is shown in phantom because visible marker 65 is located on second outer surface portion 49B of lead body 48, which is facing into the plane of the image of FIG. 2. Alternatively, visible marker 65 may be on first outer surface portion 49A. In other embodiments, visible marker 65 may be any suitable configuration (e.g., another shape, size, etc.).

In addition to or instead of visible marker 65, introducer 16 (FIG. 1) may have orientation marks to properly orient fixation elements 50, 52, and 54 of lead 14 with respect to epidermis 62 of patient 20. For example, proximal end 16A of introducer 16 may include printed markings for aligning with visible marker 65 of lead 14 to orient lead 14 such that first outer surface portion 49A faces away from epidermis 62 when lead 14 is implanted in patient 20. In some embodiments, visible marker 65 and orientation marker 45 may overlap and may effectively be a single marker.

Figure 3C:
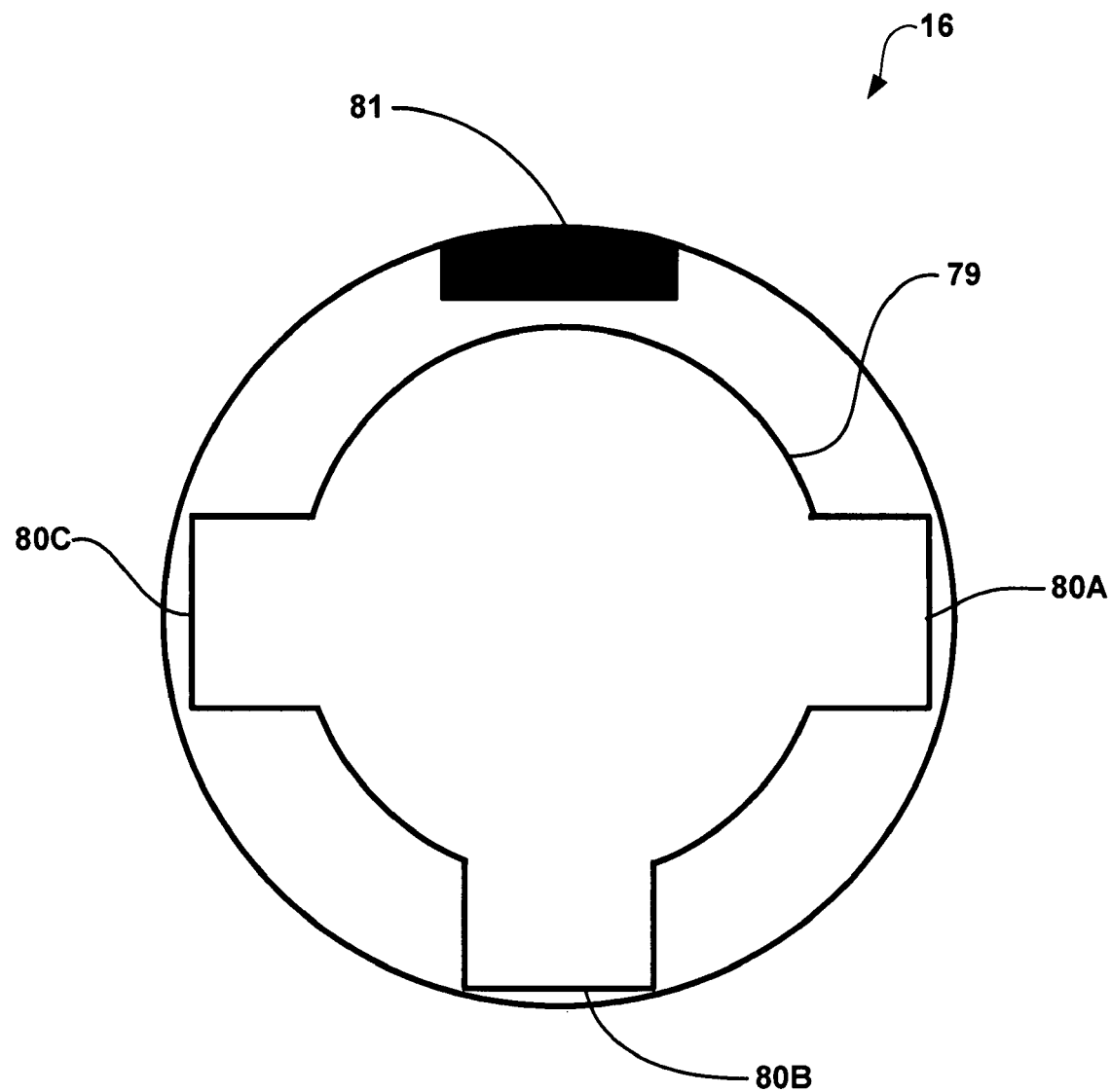
FIG. 3C is a schematic cross-sectional view of an introducer taken along line 3C-3C in FIG. 1.

FIG. 3C is a schematic cross-sectional view of introducer 16 taken along line 3C-3C in FIG. 1. In embodiments in which fixation elements 50, 52, and 54 protrude from lead body 48 during an implantation procedure, introducer 16 may be keyed to receive lead 14 in a certain orientation. In the embodiment shown in FIG. 3C, introducer 16 defines lumen 79 for receiving lead body 48, where lumen 79 defines channels 80A-C that are sized and otherwise configured to receive fixation elements 50, 52, and 54, respectively, so that lead 14 may be introduced into introducer 16 in a limited number of orientations. In this way, once introducer 16 is properly oriented with respect to epidermis 62 of patient, introducer 16 may be used to force proper orientation of lead 14 with respect to epidermis 62. Introducer 16 may be properly oriented with respect to epidermis 62 via any suitable means, such as, for example, visible or radiographic marker 81 on introducer 16. For example, when the clinician is introducing introducer 16 into patient 20, the clinician may orient introducer 16 such that visible or radiographic marker 81 is facing the clinician or facing a particular direction in order to properly orient channels 80A-C with respect to epidermis 62. In addition, channels 80A-C defined by lumen 79 of introducer 16 may help minimize the overall diameter of introducer 16, which may help minimize the invasiveness of an implantation procedure.

In addition to or instead of visible marker 65 on lead body 48 or orienting features of introducer 16, a keyed stylet may be used to guide lead 14 into an orientation that results in fixation elements 50, 52, and 54 facing away from epidermis 62. For example, just as introducer 16 is shown in FIG. 3C to be configured to receive lead 14 in one orientation, a stylet may be keyed to receive lead 14 in one orientation.

At least a longitudinally-extending section (i.e., extending in the direction between proximal end 48A and distal end 48B of lead body 48) of second outer surface portion 49B near electrodes 28 is devoid of any fixation elements or of any fixation elements that may extend into epidermis layer 62 when lead 14 is implanted in subcutaneous tissue 66. For example, in the embodiment shown in FIG. 3A, the entire second outer surface portion 49B is devoid of any fixation elements. However, in other embodiments, second outer surface portion 49B may include fixation elements sized to engage with subcutaneous tissue 66, but not epidermis 62 or dermis 64, or fixation elements to engage with dermis 64, but not epidermis 62. In another embodiment, a portion of second outer surface portion 49B other than the portion proximate to electrodes 28 may include fixation members that are the same size or greater than fixation elements 50, 52, and 54.

Figure 8:
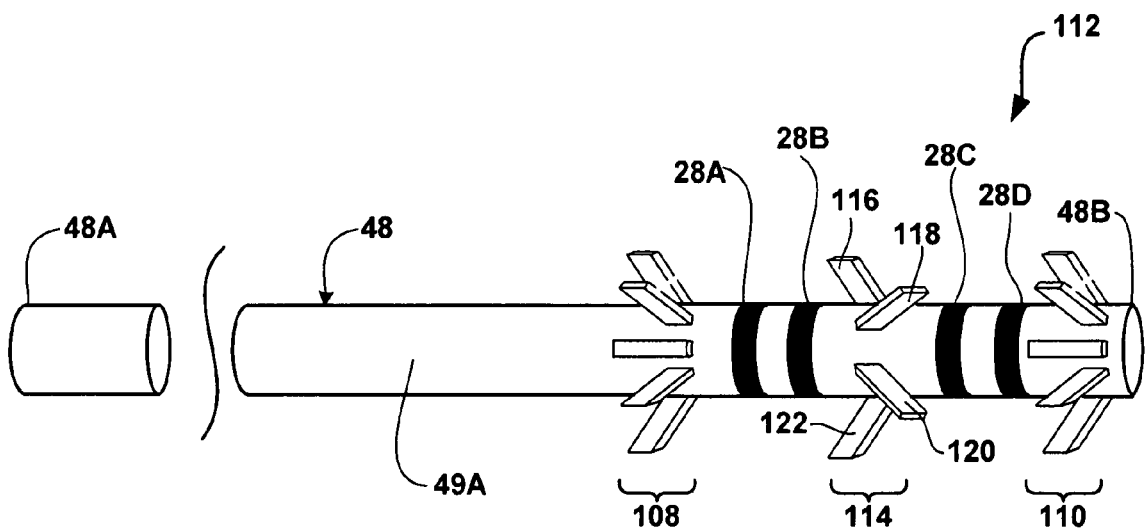

Fixation elements 50, 52, and 54 are angled toward proximal end 48A of lead body 48, which may help distal end 48B of lead body 48 resist the pulling force from proximal end 48A. However, in some applications, it may also be desirable for lead 14 to resist pulling forces from distal end 48B. Accordingly, the invention contemplates configurations of fixation elements 50, 52, and 54 that are angled both toward and away from proximal end 48A of lead body 48 (e.g., as shown in FIG. 8).

Fixation elements 50, 52, and 54 radially extend from lead body 48 at an acute angle with respect to first portion 49A. However, in other embodiments, fixation elements 50, 52, and 54 radially extend from lead body 48 at a 90° angle (e.g., as shown with respect to fixation elements 126, 128, and 130 in FIG. 9). Extending from lead body 48 at an acute angle enables fixation elements 50, 52, and 54 to engage with surrounding tissue to prevent both axial and radial movement of lead body 48.

FIG. 3B is a schematic cross-sectional view of lead 14 taken along line 3B-3B in FIG. 3A. Lead body 48 carries a plurality of conductors 74 (shown in FIG. 3B as a single conductive center of lead body 48 for clarity of illustration) for electrically coupling electrodes 28 (FIG. 3A) to therapy delivery module 40 of neurostimulator 12 (FIG. 2). Typically, a separate conductor electrically couples each electrode 28A-D to therapy delivery module 40. Separate conductors permit independent selection of individual electrodes 28A-D. Furthermore, each of the conductors electrically coupled to separate electrodes 28A-D are electrically insulated from each other. Insulating layer 76 surrounds conductors 74 in order to electrically insulate conductors 74 from subcutaneous tissue 66 when lead 14 is implanted in patient 20 and to help protect a clinician who may be handling lead 14 from shock.

As previously described, each of fixation elements 50, 52 or 54 may be directly coupled to lead body 48, as shown in FIG. 3B, or indirectly coupled to lead body 48 (e.g., carried by a fixation sleeve). In the embodiment shown in FIG. 3B, fixation elements 50, 52 or 54 are each attached to lead body 48 with an adhesive. For example, adhesive 78 is disposed between fixation element 54 and lead body 48.

As FIGS. 3A and 3B illustrate, when lead 14 is implanted in subcutaneous tissue 66, fixation elements 50 and 54 extend from lead body 48 substantially parallel to epidermis layer 62, while fixation element 52 extends away from epidermis layer 62. Implanting lead 14 within subcutaneous tissue 66 such that one or more fixation elements 50, 52 or 54 extended through dermis layer 64 or even epidermis layer 66 may increase discomfort to patient 20. In addition, one or more fixation elements 50, 52 or 54 may be visible (e.g., a protrusion may be seen protruding into epidermis 62). Discomfort to patient 20 may be attributable to the one or more fixation elements 50, 52 or 54 causing stress points at the interface between the one or more fixation elements 50, 52 or 54 and dermis layer 64, or even epidermis layer 62. In addition, fixation elements 50, 52 or 54 may rub against dermis layer 64 and/or even epidermis layer 62, which may lead to erosion of and possible damage to dermis layer 64 and/or epidermis layer 62. As discussed, in the embodiment of lead 14 shown in FIGS. 3A-3B, second outer surface portion 49B is devoid of fixation elements. As a result, second outer surface portion 49B provides a relatively smooth surface for interfacing with epidermis layer 62 or dermis layer 64. Thus, in some applications, such as when lead 14 is implanted in subcutaneous tissue 66, it may be desirable for lead 14 to be implanted in a specific orientation.

Figure 4A:
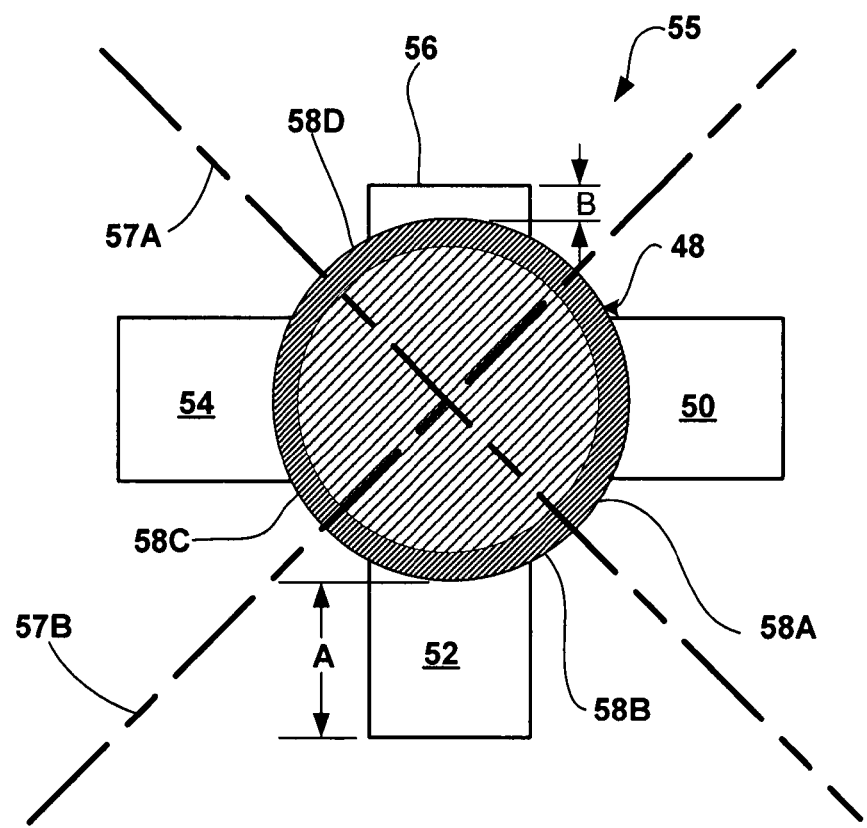
FIGS. 4A-4B are schematic cross-sectional views of alternate embodiments of implantable medical leads including fixation elements along a first outer surface portion of the lead body.

In some embodiments, second outer surface portion 49B may include structural fixation elements that also engage with surrounding tissue to prevent migration of lead 14. However, these fixation elements do not extend as far from second outer surface portion 49B as fixation elements 50, 52 or 54 extend from first portion 49A in order to minimize the extent to which the fixation elements on second portion 49B engage with epidermis layer 62 or dermis layer 64. FIG. 4A is a schematic cross-sectional view of lead 55 including fixation element 56 extending from second outer surface portion 49B of lead body 48. As FIG. 4A illustrates, fixation element 56 is relatively small compared to fixation elements 50, 52, and 54. Fixation element 56 does not extend as far from lead body 48 as fixation elements 50, 52, and 54. In particular, in the embodiment shown in FIG. 4A, fixation element 52 (as well as fixation elements 50 and 54) extends a distance A from outer surface 49 of lead body 48, while fixation element 56 extends a distance B from outer surface 49 of lead body 48. Distance B of fixation element 56 may be selected such that fixation element 56 engages with subcutaneous tissue 66, rather than epidermis layer 62 or dermis layer 64, when lead 55 is implanted in subcutaneous tissue 66 of patient 20 and oriented such that first outer surface portion 49A faces away from epidermis layer 66.

Also shown in FIG. 4A are lines 57A and 57B, which are shown to demonstrate that lead body 48 defines four quadrants 58A-D. Rather than describing the arrangement of fixation elements 50, 52, 54, and 56 about lead body 48 with respect to first and second outer surface portions 49A and 49B (FIG. 3B), respectively, the arrangement of fixation elements 50, 52, 54, and 56 may also be described with respect to quadrants 58A-D of lead body 48. In the embodiment of lead 55 shown in FIG. 4A, fixation element 50 extends from first quadrant 58A of lead body 48, fixation element 52 extends from second quadrant 58B, third fixation element 54 extends from third quadrant 58C, and fixation element 56 extends from fourth quadrant 58D. Fixation element 56 extending from fourth quadrant has a smaller cross-sectional profile than fixation elements 50, 52, and 54.

Lead body 48 also defines quadrants 58A-D in each of the schematic cross-sectional views shown in FIGS. 3B, 4B, 5B, 6B, 10B, and 11. However, for clarity of illustration and description, quadrants are not labeled in FIGS. 3B, 4B, 5B, 6B, 10B, and 11. Each of the leads shown in FIGS. 3B, 4B, 5B, 6B, 10B, and 11 may be described with respect to quadrants 58A-D. For example, lead 14 shown in FIG. 3B includes fixation element 50 extends from first quadrant 58A of lead body 48, fixation element 52 extends from second quadrant 58B, and third fixation element 54 extends from third quadrant 58C, while fourth quadrant 58D is devoid of any fixation elements.

Figure 4B:
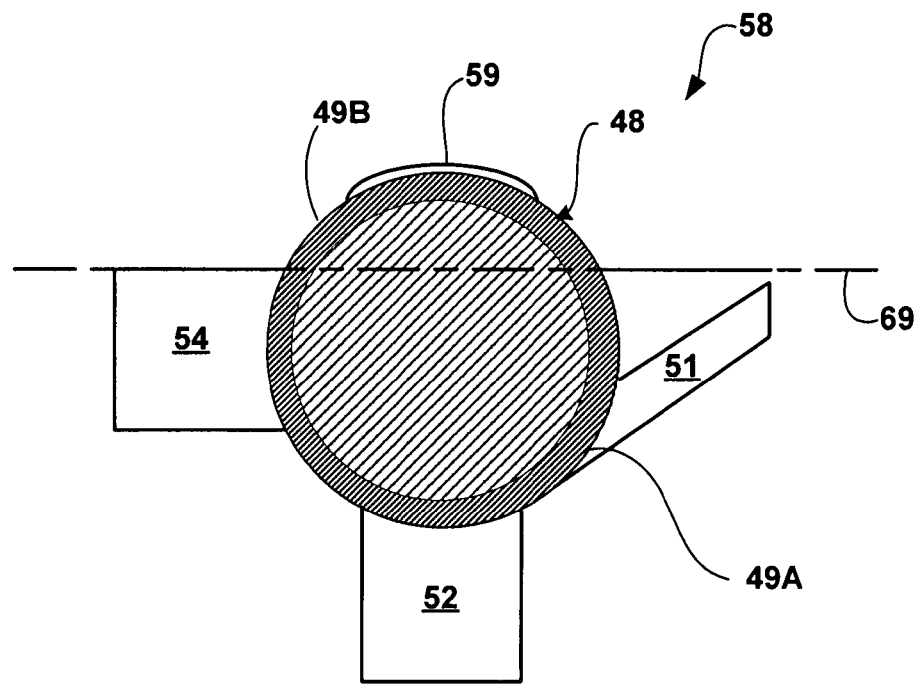

In yet another embodiment, second outer surface portion 49B may include a non-structural fixation element, such as a surgical adhesive. FIG. 4B is a schematic cross-sectional view of lead 58 including adhesive layer 59 along second outer surface portion 49B of lead body 48, and fixation elements 51, 52, and 54 along first outer surface portion 49A. As FIG. 4B illustrates, adhesive layer 59 does not protrude from second portion 49B of adhesive layer to the extend fixation elements 50, 52, and 54 protrude from first portion 49A. In another embodiment, an adhesive may be embedded in second portion 49B of lead body 48, rather than being a separate adhesive layer 59. Regardless of the type of fixation element, if any, carried by second outer surface portion 49B, it is desirable to minimize the extent to which the fixation element along second outer surface portion 49B engages with and protrudes into epidermis layer 62 or dermis layer 64 in order to increase the comfort to patient 20.

Adhesive layer 59 may be, for example, surgical adhesive elements disposed on or embedded with second outer surface portion 49B of lead body 48. Examples of suitable adhesive elements are discussed in commonly assigned U.S. patent application Ser. No. 11/591,443 by Martin T. Gerber, entitled "IMPLANTABLE MEDICAL ELONGATED MEMBER WITH ADHESIVE ELEMENTS" and filed on the same date as the present disclosure, which is hereby incorporated by reference in its entirety. The adhesive properties of adhesive layer 59 may be activated by any suitable means, including exposure to fluids, a certain temperature, or by activating agents. For example, adhesive layer 59 may be separated from surrounding tissue by a sheath until lead 14 reaches a targets stimulation site, at which time a clinician may withdraw the sheath to expose adhesive layer 59 to surrounding tissue, which may activate adhesive layer 59 via moisture, temperature or otherwise.

Fixation element 51 of lead 58 is disposed on first outer surface portion 49A, but extends in a superficial direction toward epidermis 62 when lead 58 is implanted in patient such that first outer surface portion 49A faces a deep direction. Although fixation element 51 extends toward epidermis 62, fixation element 51 does not contact epidermis 62 because of its placement on first outer surface portion 49A. In particular, fixation element 51 does not extend as far demarcation line 69 separating first and second outer surface portions 49A and 49B, respectively.

While lead 14 includes three fixation elements 50, 52, and 54 spaced about 90° with respect to each other about lead body 48, and particularly, on first outer surface portion 49A, in other embodiments, a lead may include any suitable number of fixation elements in any suitable arrangement about the lead body. These and other embodiments of leads including alternate numbers and/or arrangements of fixation elements are shown in FIGS. 5A-13B and described in reference thereto. For clarity of description, like numbered reference numbers designate substantially similar elements throughout FIGS. 2-12. In FIGS. 1-13B, the components of the leads, as well as any other components that may be illustrated, are not necessarily drawn to scale. For example, each of the hydrogel fixation members 50, 52, and 54 shown in FIGS. 2-4B are not necessarily drawn in correct proportion to the length or diameter of lead body 48.

Figure 5A:
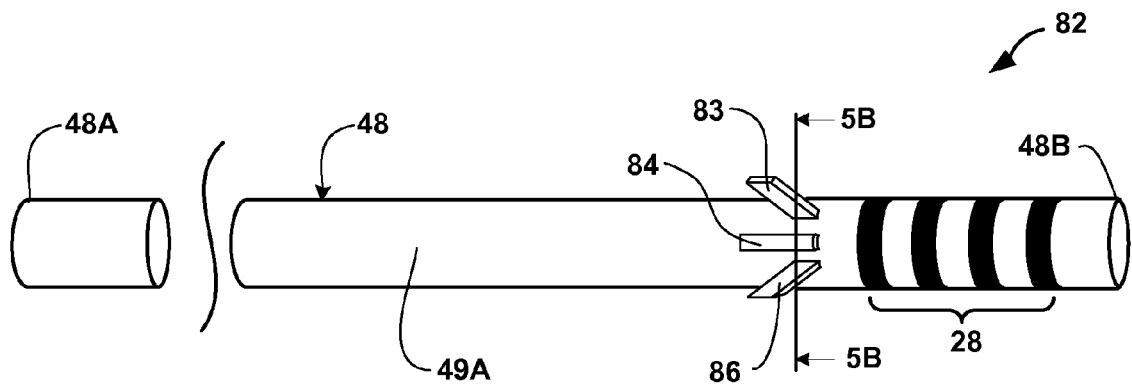
FIGS. 5A-8 illustrate alternate arrangements of fixation elements on a lead body.
Figure 5B:
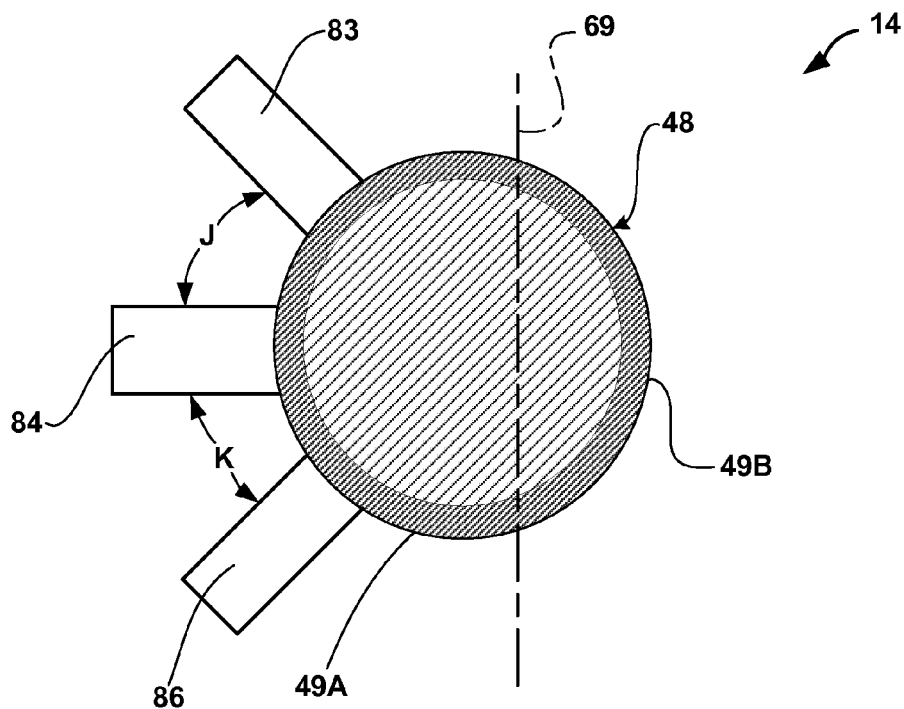

FIGS. 5A and 5B are a perspective view and schematic cross-sectional view, respectively, of lead 82, which includes fixation elements 83, 84, and 86 disposed between proximal end 48A and electrodes 28 for fixing lead 82 proximate to target stimulation site 18. As previously described, proximal end 48A of lead body typically includes contacts (not shown in FIG. 5A), for electrically connecting electrodes 28 of lead 82 with a neurostimulator (e.g., neurostimulator 12 in FIG. 1A), a lead extension or other medical device. Fixation elements 83, 84, and 86 are coupled to first outer surface portion 49A of outer surface 49 of lead body 48. In FIG. 5A, first outer surface portion 49A is shown, while second outer surface portion 49B faces into the plane of the image of FIG. 5A. In FIG. 5B, line 69 indicates the demarcation between first outer surface portion 49A and second outer surface portion 49B.

As FIG. 5B illustrates, fixation elements 83 and 84 are spaced about angle J with respect to each other about the outer perimeter of lead body 48, while fixation elements 84 and 86 are spaced about angle K with respect to each other. Angles J and K may, but need not be equal. In contrast to fixation elements 50, 52, and 54 of lead 14 (FIGS. 2-4B), fixation elements 83, 84, and 86 are spaced less than about 90° with respect to each other about first portion 49A of lead body 48. For example, angles J and K may each be about 45°. As a result of the arrangement of fixation elements 83, 84, and 86 about first outer surface portion 49A of lead body 48, when lead 82 is implanted in subcutaneous tissue 66 (FIG. 3A), fixation elements 83, 84, and 86 extend away from epidermis layer 62. Thus, neither fixation element 83, 84 or 86 radially extend from first portion 49A lead body 48 in a direction that results in fixation element 83, 84 or 86 that are substantially parallel to epidermis layer 62, as with fixation elements 50 and 54 of lead 14 (FIGS. 2-3B).

First outer surface portion 49A of the lead body 48 of each of leads 14 and 82 both include one set of fixation elements (i.e., a group of fixation elements that substantially share an axial position with respect to lead body 48) located proximal to electrodes 28. In other embodiments, a lead may include more than one set of fixation elements, and the fixation elements may be otherwise arranged, such as between electrodes 28, distal to electrodes 28, or combinations thereof. Examples of these embodiments are shown in FIGS. 6A-8.

Figure 6A:
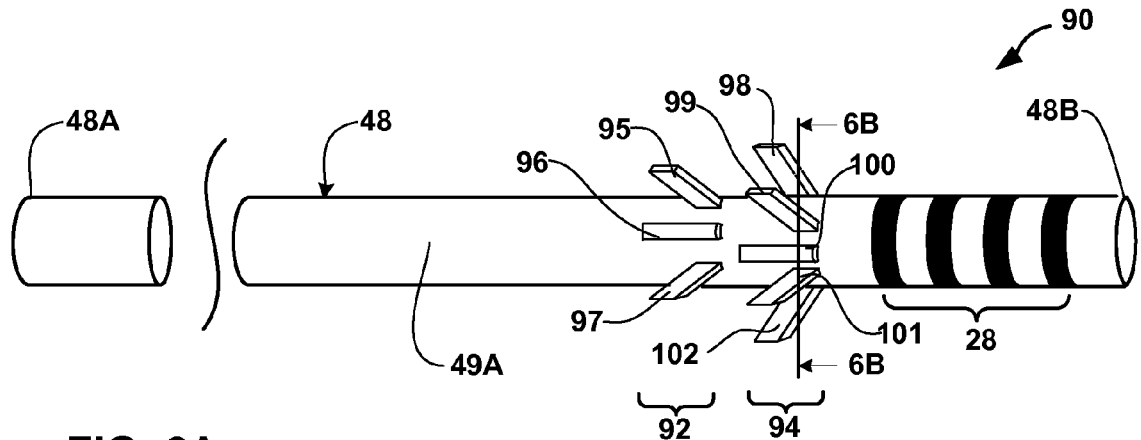
Figure 6B:
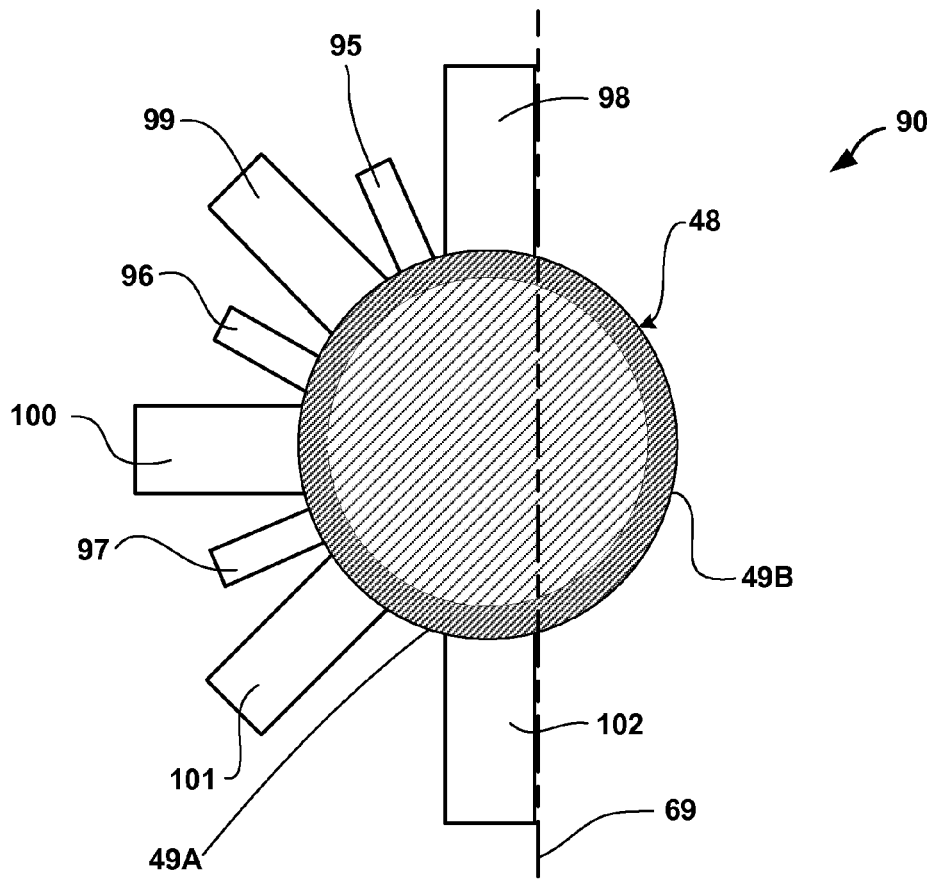

FIGS. 6A and 6B are a perspective view and schematic cross-sectional view of lead 90, which includes two sets 92 and 94 of fixation elements on first outer surface portion 49A that are axially displaced from each other with respect to lead body 48. First set 92 include fixation elements 95-97, and second set 94 includes fixation elements 98-102. As shown in FIG. 6B, in the cross-sectional view of lead 90, the fixation elements 95-102 do not overlap. Thus, fixation elements 95-97 of first set 92 each have different radial locations about first outer surface portion 49A than fixation elements 98-102 of second set 94. Accordingly, fixation elements 95-102 each extend from first outer surface portion 49A of lead body 48 in different radial directions.

Figure 7:
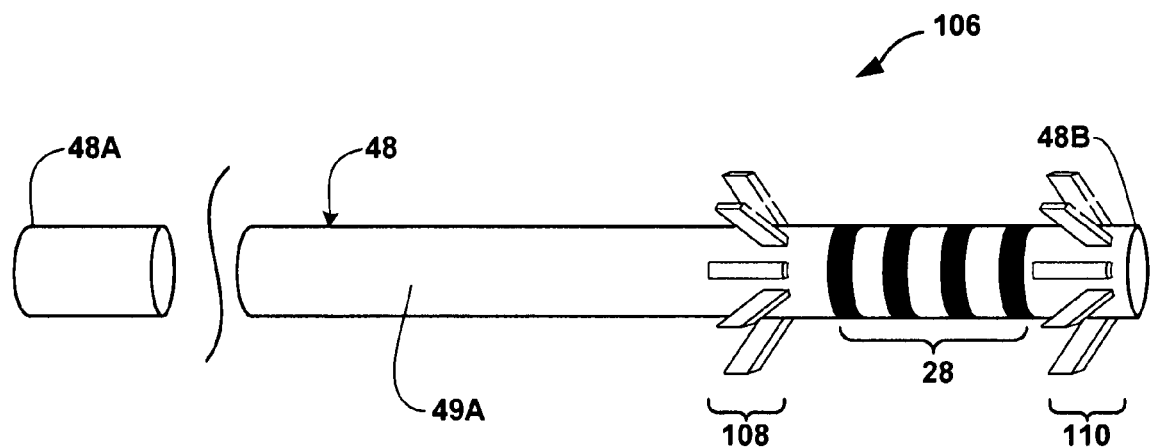

First and second sets 92 and 94 of fixation elements are shown proximate to electrode 50. However, as shown in FIG. 7, lead 106 may include first set 108 of fixation elements separated from second set 110 of fixation elements by electrodes 28. First and second sets 108 and 110 of fixation elements are each disposed along first outer surface portion 49A of lead body 48. In the embodiment of lead 106 shown in FIG. 7, first and second sets 108 and 110 of fixation elements, which may each include any suitable number of fixation elements, may be located proximate and distally, respectively, with respect to electrodes 28. While both leads 14 (FIGS. 3A-3) and 106 include fixation elements for fixing leads 14 and 106, respectively, to target stimulation site 18 (FIG. 1), which may be within subcutaneous tissue 66 (FIG. 3A), lead 106 may be useful for locally fixing distal end 48B of lead body 48. In some applications of therapy system 10 (FIGS. 1 and 2), such as when therapy system 10 is used to stimulate a pudendal nerve, it may be desirable to locally fix distal end 48B of lead body 48.

FIG. 8 is a perspective view of yet another embodiment of lead 112 in accordance with the invention. In addition to first and second sets 108 and 110 of fixation elements along first outer surface portion 49A of lead body 48, lead 112 includes third set 114 of fixation elements between electrodes 28B and 28C. Third set 114 includes fixation elements 116, 118, 120, and 122. In other embodiments, lead 112 may include a set of fixation elements between all of electrodes 28 or between any other combination of electrodes (e.g., between electrodes 28A and 28B).

While each of leads 14, 82, 90, and 106 of FIGS. 3A, 5A, 6A, and 7 include fixation elements angled toward proximal end 48A of lead body 48, in other embodiments, the fixation elements may also be angled toward distal end 48B of lead body 48. For example, fixation elements 116 and 122 of third set 114 of fixation elements of lead 112 shown in FIG. 8 are angled toward proximal end 48A of lead body 48, while fixation elements 118 and 120 are angled toward distal end 48B.

Figure 9:
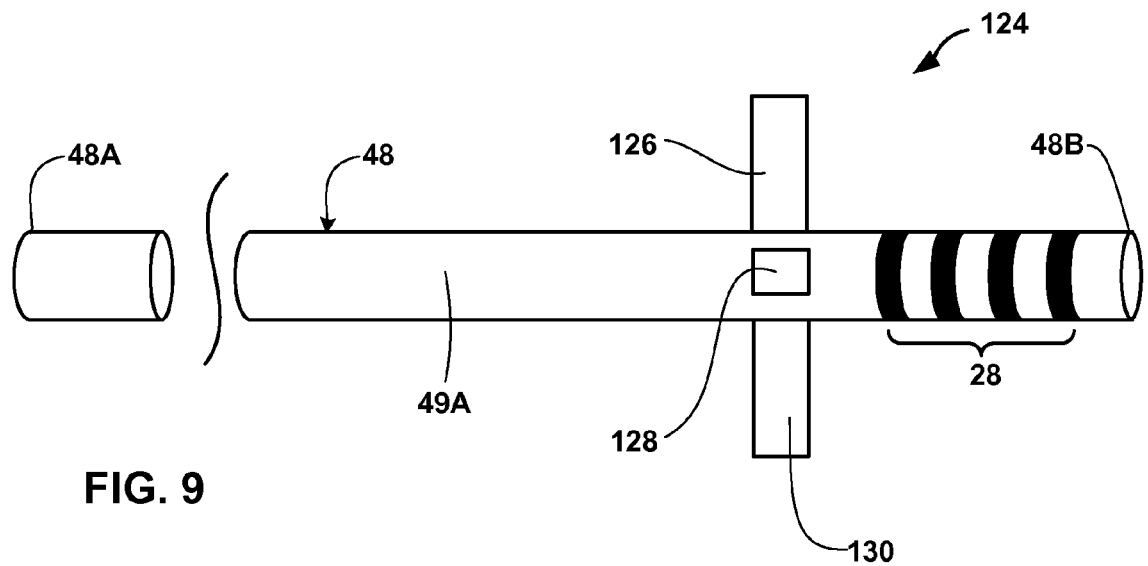
FIG. 9 is a perspective view of a lead including fixation elements extending radially outward from a lead body at approximately 90° with respect to a first outer surface portion of the lead body.

Fixation elements 116, 118, 120, and 122 each extend from lead body 48 at an acute angle with respect to first portion 49A of lead body 48. As previously discussed, fixation elements of a lead in accordance with the invention may also extend radially outward at about 90° with respect to first portion 49A of lead body 48. An embodiment of such a lead is shown in FIG. 9, which is a perspective view of lead 124 including fixation elements 126, 128, and 130 that extend radially outward at approximately 90° with respect to first outer surface portion 49A of lead body 48.

Figure 10A:
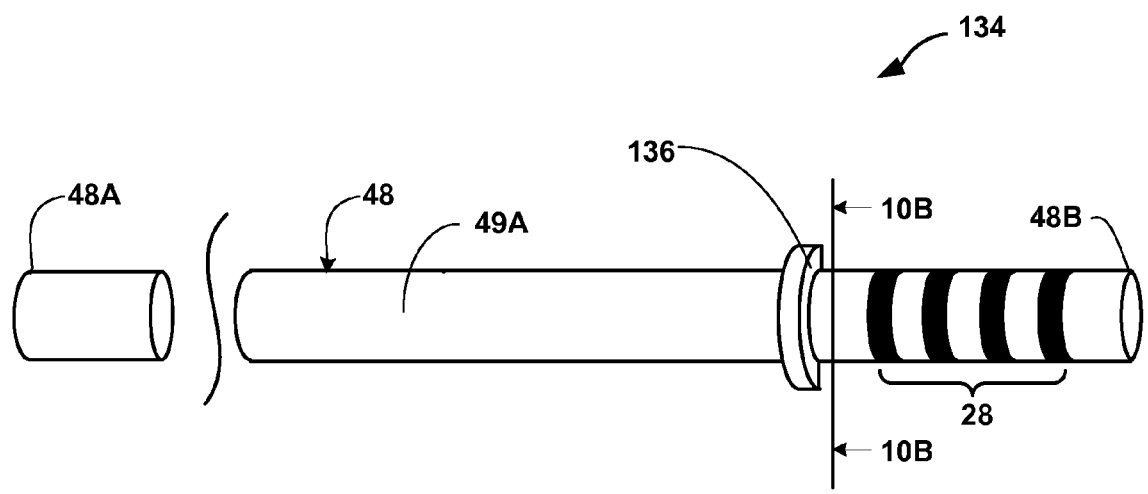
FIGS. 10A and 10B are a perspective view and schematic cross-sectional view, respectively, of a lead including a fixation element extending around a first outer surface portion of a lead body.
Figure 10B:
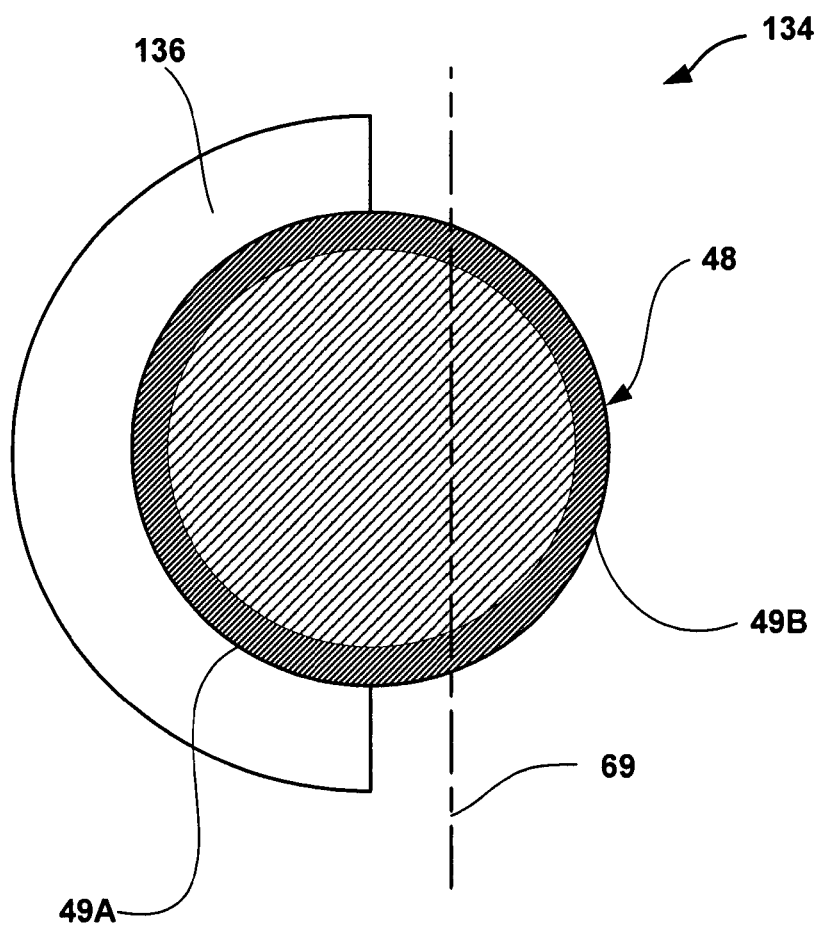

While tine-shaped fixation elements are shown in FIGS. 2-9 above, a fixation element may have any suitable shape. FIGS. 10A and 10B are a perspective view and cross-sectional view, respectively, of lead 134, which includes fixation element 136 that extends around first outer surface portion 49A of lead body 48. Although fixation element 136 is shown in FIGS. 10A and 10B as expanding radially outward without an angular component (i.e. at 90° with respect to first outer surface portion 49A), in alternate embodiments, fixation element 136 may extend from lead body 48 at an angle with respect to first portion 49A.

As shown in FIGS. 10A and 10B, a single fixation element 136 is disposed between electrodes 28 and proximal end 48A of lead body 48. In alternate embodiments, lead 134 may include any suitable number of fixation elements that extend around first outer surface portion 49A of lead body 48 and/or fixation element 134 may be used in combination with tine-like or other fixation members that do not extend around first outer surface portion 49A of lead body 48. For example, in another embodiment, fixation member 136 may extend around 25%, 50% or 75% of the outer perimeter of first outer surface portion 49A of lead body 48. For example, FIG. 11 shows a schematic cross-sectional view of lead 138, which includes fixation element 140 extending around about 75% of first outer surface portion 49A of lead body 48.

In each of leads 14, 82, 90, 106, 112, 124, 134 of FIGS. 3A, 5A, 6A, 7-9, respectively, lead body 48 is cylindrical and defines first outer surface portion 49A carrying fixation elements, while second outer surface portion 49B is devoid of any fixation elements or includes one or more fixation elements that do not engage with epidermis 62 (FIG. 3A) when lead 14 is implanted in subcutaneous tissue 66. In another embodiment, a lead may include a paddle shape (i.e. a paddle lead) and may include fixation elements along one surface of the paddle lead, to thereby define a paddle lead including interior fixation when the paddle lead is implanted in subcutaneous tissue 66 (FIG. 2) of patient 20 or near occipital region 29 (FIG. 1) of patient 20.

Figure 12A:
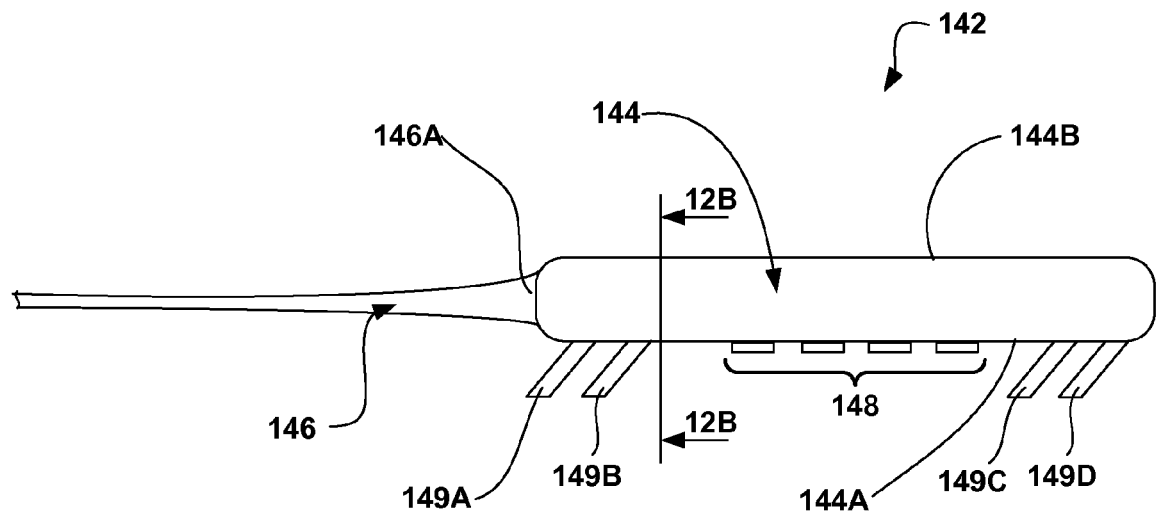
FIG. 12A is a side view of a paddle lead including fixation elements along a first outer surface portion.
Figure 12B:
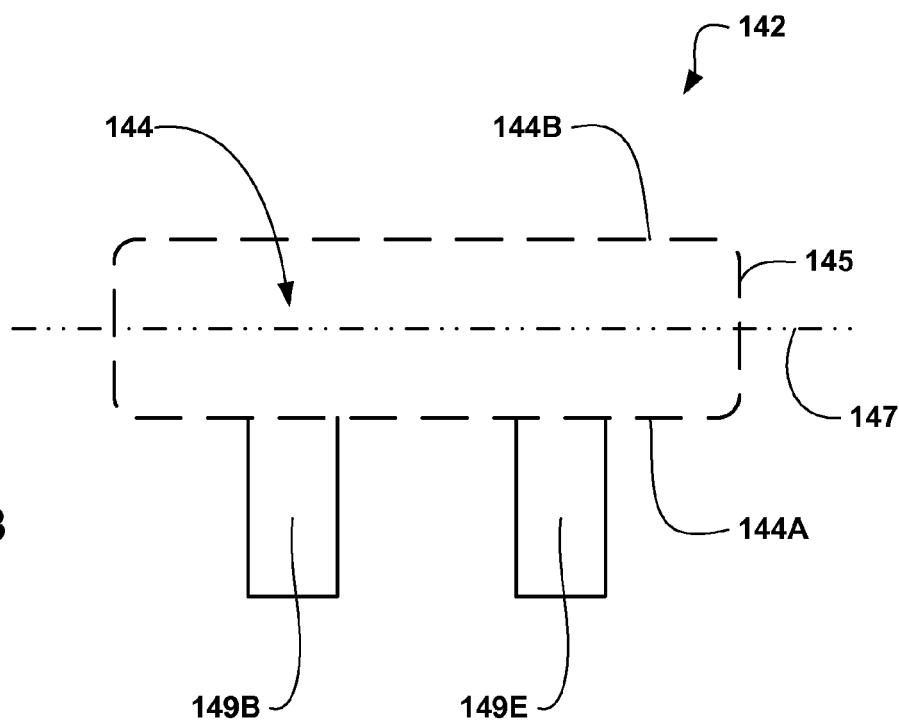
FIG. 12B is a schematic cross-sectional view of a lead body of a paddle lead taken along line 12B-12B in FIG. 12A.

FIGS. 12A and 12B are a side view and a schematic cross-sectional view of paddle lead 142, respectively, which includes substantially flat, paddle-like shaped lead body 144 coupled to distal end 146A of lead body connector 146. A proximal end (not shown in FIG. 12A) of lead body connector 146 may be mechanically coupled to a neurostimulator (e.g., neurostimulator 12 of FIGS. 1 and 2) or another medical device. Lead body 144 defines a "paddle" like shape, including first surface 144A and second surface 144B, which is opposite first surface 144A. As shown in FIG. 12B, which is a schematic cross-sectional view of lead body 144 taken along line 12B-12B in FIG. 12A, lead body 144 defines an outer perimeter 145 (shown in phantom lines). Line 147 demarcates first and second surfaces 144A and 144B, respectively, which each extend around about fifty percent of outer perimeter 145 of lead body 144.

In the embodiment shown in FIG. 12A, electrodes 148 are carried by first surface 144A of lead body 144. In another embodiment, paddle lead 142 may also include electrodes along second surface 144B of lead body 144. Each of electrodes 148 may be electrically coupled to the neurostimulator, lead extension or other medical device via electrical conductors disposed within lead body connector 146. A proximal end (not shown in FIG. 12A) of lead body connector 146 may include electrical contacts for electrically connecting the electrical conductors within lead body connector 146 with the neurostimulator.

First surface 144A of lead body 144 includes fixation elements 149A-E, while second surface 144B is devoid of any fixation elements. In the embodiment shown in FIG. 12A, fixation elements 149A-D are tine-like structures that are angled toward lead body connector 146. In other embodiments, fixation elements 149A-D on first surface 144A of paddle lead body 144 may be any suitable shape or type of fixation element, and may extend from first surface 144A at any suitable angle (e.g., radially outward or away from lead body connector 146).

When paddle lead 142 is implanted in patient 20, lead 142 may be oriented such that first surface 144A, and accordingly fixation elements 149A-D, faces away from epidermis 62, scalp 30 or another integumentary layer of patient 20 in order to help minimize or eliminate any discomfort or irritation to patient attributable to fixation elements 149A-D. Second surface 144B of lead body 144 provides a relatively smooth surface for interfacing with epidermis 62 (FIG. 2) or scalp 30 of patient 20 because second surface 144B does not have any fixation elements that may engage with epidermis 62 or scalp 30 to create points of stress.

Figure 13A:
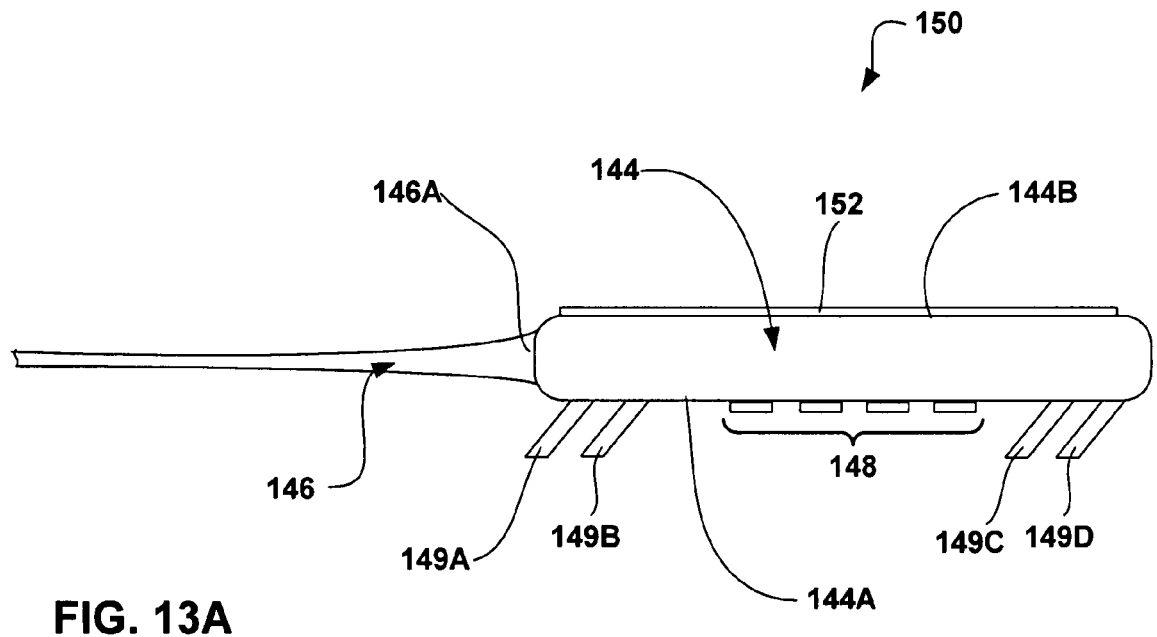
FIGS. 13A and 13B are side views of alternate embodiments of a paddle lead including fixation elements along both the first outer surface portion and the second outer surface portion.

FIG. 13A is a side view of another embodiment of paddle lead 150, which includes substantially flat, paddle-like shaped lead body 144 coupled to distal end 146A of lead body connector 146 and electrodes on first surface 144A of lead body 144. In addition to fixation elements 149A-D on first surface 144A of lead body 144, lead 150 includes fixation element 152 on second surface 144B of lead body 144. In particular, fixation element 152 is a layer of surgical adhesive that helps prevent migration of lead 150 following implantation in patient 20. Alternatively, surgical adhesive layer 152 may be adhesive elements disposed on or embedded with second surface 144B of lead body, as discussed by commonly assigned U.S. patent application Ser. No. 11/591,443 by Martin T. Gerber, entitled "IMPLANTABLE MEDICAL ELONGATED MEMBER WITH ADHESIVE ELEMENTS" and filed on the same date as the present disclosure, which is hereby incorporated by reference in its entirety.

Figure 13B:
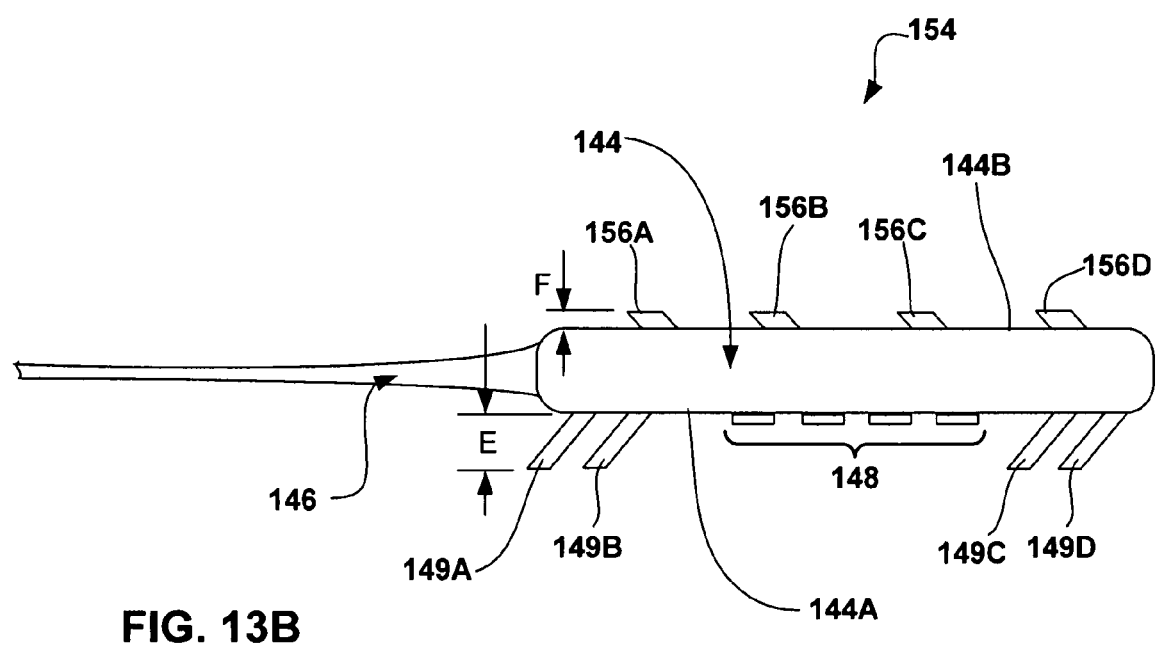

FIG. 13B is a side view of another embodiment of paddle lead 154, which includes fixation elements 156A-D along second surface 144B of lead body 144. Fixation elements 149A-D as well as fixation elements 156A-D may engage with surrounding tissue to help substantially fix a position of lead 154 proximate to target stimulation site 18. In the embodiment shown in FIG. 13B, fixation elements 156A-D are tine-like structures that are angled toward lead body connector 146. In other embodiments, fixation elements 156A-D on second surface 144B of paddle lead body 144 may be any suitable shape or type of fixation element (e.g., one or more balloon fixation elements) and may extend from second surface 144B at any suitable angle (e.g., radially outward or away from lead body connector 146).

Fixation elements 156A-D do not extend from second surface 144B of lead body 144 to the extent that fixation elements 149A-D extend from first surface 144A of lead body 144. That is, in FIG. 13A, dimension E, which is the overall distance each of fixation elements 149A-D extend from first surface 144A of lead body 144 is greater than dimension F, which is the overall distance each of fixation elements 156A-D extend from second surface 144B. Dimension F is selected such that fixation elements 156A-D do not engage with and protrude into an integumentary layer (e.g., epidermis layer 62 (and in some cases, dermis layer 64) or scalp 30 (FIG. 1)) of patient 20 when lead 154 is implanted in patient 20 such that first surface 144A of lead body 144 faces away from the integumentary layer. The selective sizing of fixation elements 156A-D may thus help minimize any discomfort to patient 20 that is attributable to fixation elements 156A-D.

Figure 14:
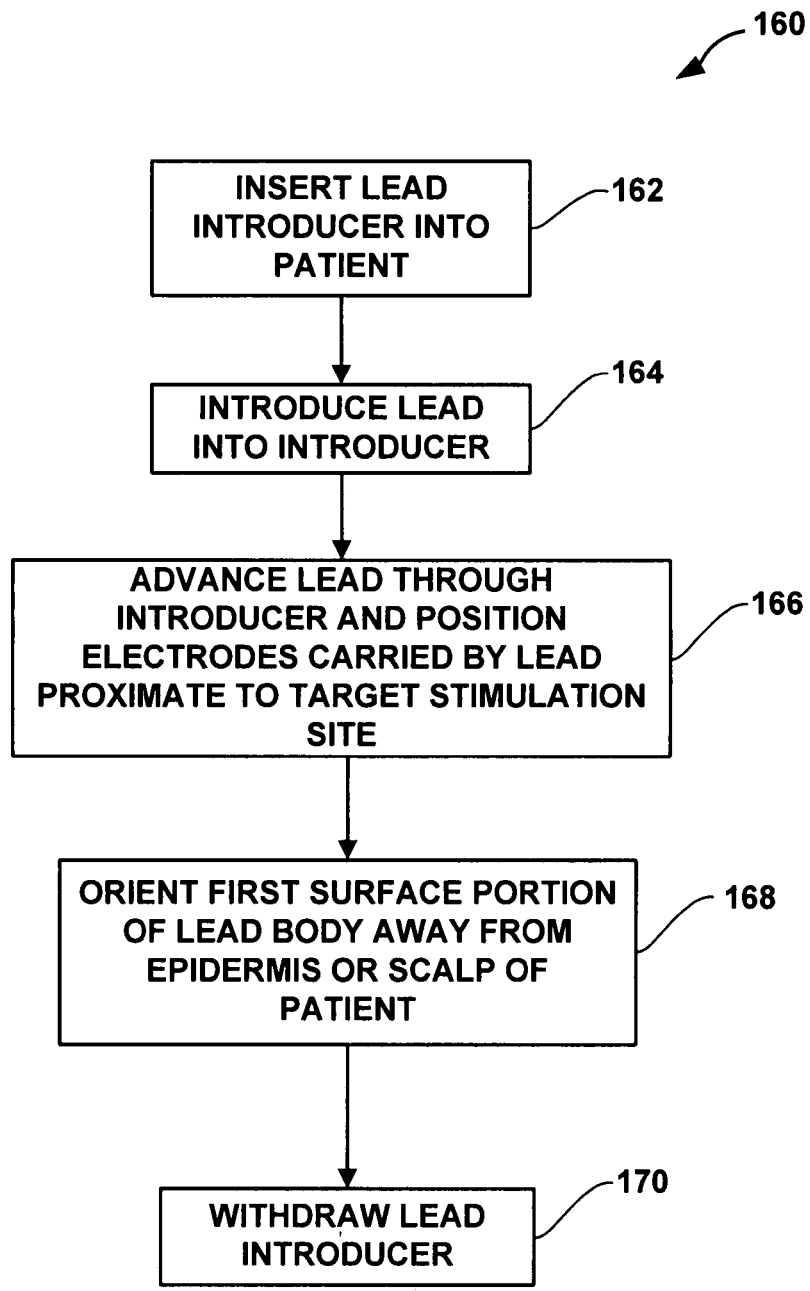
FIG. 14 is a flow diagram illustrating one example method for implanting a lead including fixation members along a first outer surface portion in accordance with an embodiment of the present invention.

FIG. 14 is a flow diagram of process 160 for implanting a lead 14 (FIGS. 1-3B) including fixation elements along first surface 49A of lead body 48 in accordance with the invention. While lead 14 is referenced in the description of FIG. 14, it should be understood that process 160 may be used to implant any of leads 82, 90, 106, 112, 124, 134, and 138 of FIGS. 5A, 6A, 7, 8, 9, 10A, and 11, respectively, or any other lead including fixation elements disposed along a portion (e.g., first portion 49A) of an outer surface of lead body 48 in accordance with the invention. Furthermore, while implantation of lead 14 into subcutaneous tissue 66 (FIG. 3A) of patient 20 is described, in other embodiments, lead 14 may be implanted proximate to any suitable target therapy delivery site in patient 20.

A lead introducer, such as an introducer needle, is introduced into epidermis layer 62 (FIG. 3A) of patient 20 (FIG. 1) and a distal end of the introducer is guided into subcutaneous tissue 66 proximate to nerve 68 (162). The introducer needle may be inserted into the patient percutaneously or via an incision (e.g., incision 33 in FIG. 1) in epidermis layer 62. Lead 14 is introduced into a lumen of the introducer (164). In particular, distal end 14B of lead 14 is introduced into the lumen before proximal end 14A.

Lead 14 is advanced through the lumen until electrodes 28 adjacent to distal end 48B of lead body 48B of lead 14 are positioned proximate to nerve 68 (166). For example, distal end 14B of lead 14 may be advanced through the lumen of the introducer until at least distal end 14B protrudes past the lumen and into tissue of patient 20 and fixation elements 50, 52, and 54 are deployed from the introducer (i.e., are advanced past a distal end of the introducer). Alternatively, fixation elements 50, 52, and 54 may be deployed from the introducer by withdrawing the introducer or another sheath separating fixation elements 50, 52, and 54 from tissue of patient 20, thereby exposing lead 14.

If necessary, lead 14 is oriented (e.g., rotated) such that first outer surface portion 49A of lead body 48 faces away from epidermis layer 62 (168). Lead 14 may be oriented prior to or subsequent to positioning electrodes 28 proximate to nerve 68 (166). Positioning of the introducer and/or orientation and positioning of lead 14 may be aided by imaging techniques, such as by fluoroscopy using markers (e.g. radio-opaque or otherwise visible) on lead body 48. The markers may help indicate a location of fixation elements 50, 52, and 54 with respect to the introducer needle. Alternatively, lead 14 may be oriented using visible marker 65 (FIG. 2) and/or a stylet or introducer 16 may include features (e.g., channels for receiving fixation elements 50, 52, and 54) for orienting lead 14 such that first outer surface portion 49A of lead body 48 faces away from epidermis 62 when lead 14 is implanted in patient 20.

Upon deployment into body tissue, fixation elements 50, 52, and 54 engage with surrounding subcutaneous tissue 66 to substantially fix electrodes 28 within subcutaneous tissue 66 proximate to nerve 68. After lead 14 is positioned, the lead introducer is withdrawn from patient 20 (170). If an adhesive is also used to help prevent migration of lead 14 after implantation in patient 20 (e.g., an adhesive disposed along second outer surface portion 49B of lead body 48), the adhesive may begin reacting with surrounding tissue or otherwise activating upon deployment into body tissue.

A lead including a vacuum cavity for receiving tissue may be useful for various electrical stimulation systems. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity.

In addition, the fixation element arrangement described herein with respect to leads 14, 82, 90, 106, 112, 124, 134, and 138 may also be useful for fixing a catheter, such as a drug deliver catheter, proximate to a target drug delivery site.

Various embodiments of the invention have been described. These and other embodiments are within the scope of the following claims.

The invention claimed is:

1. A method comprising:
   introducing a medical elongated member into a body of a patient;
   advancing the medical elongated member to a target tissue site proximate to at least one of an occipital nerve or a trigeminal nerve within the body of the patient, wherein the elongated member defines an outer surface comprising a first outer surface portion and a second outer surface portion extending around at least approximately ten percent of an outer perimeter of the elongated member, the first and second outer surface portions being aligned at and sharing an axial position along a longitudinal axis or the elongated member, and the elongated member further comprising a first fixation element extending a first distance from the first outer surface portion and a second fixation element extending a second distance from the second outer surface portion, the first distance being greater than the second distance, and wherein a longitudinally-extending section of the second outer surface portion proximate to a distal end of the elongated member is substantially devoid of any fixation elements that extend the first distance from the second outer surface portion; and
   orienting the second fixation element in a substantially superficial direction.

2. The method of claim 1, wherein advancing the medical elongated member to the target tissue site comprises positioning the medical elongated member within subcutaneous tissue of the patient superior to the at least one of the occipital nerve or the trigeminal nerve.

3. The method of claim 1, wherein orienting the second fixation element in a substantially superficial direction comprises orienting the second outer surface portion in a superficial direction.

4. The method of claim 1, further comprising aligning a visible marker on the elongated member with respect to an epidermis of the patient, wherein the visible marker comprises at least one of a printed marking on the elongated member, an indentation in the elongated member or a radiographic marker.

5. The method of claim 1, wherein introducing the medical elongated member into the patient comprises:
   introducing an introducer into the body of the patient superior to a fascia layer; and
   introducing the medical elongated member into a lumen of the introducer.

6. The method of claim 5, further comprising aligning a visible marker of the introducer with respect to an epidermis of the patient.

7. The method of claim 5, wherein introducing the medical elongated member into a lumen of the introducer comprises aligning the first fixation element with a channel defined by the lumen.

8. The method of claim 1, wherein the second outer surface portion of the medical elongated member extends around at least approximately twenty-five percent of the outer perimeter of the medical elongated member.

9. The method of claim 1, wherein the medical elongated member comprises at least one of a lead comprising at least one electrode or a catheter.

10. The method of claim 9, wherein the medical elongated member comprises the lead, and the first fixation element is located between the electrode and a proximal end of the elongated member and the medical elongated member further comprises a third fixation element located between the electrode and a distal end of the medical elongated member.

11. The method of claim 9, wherein the medical elongated member comprises the lead and the at least one electrode comprises a plurality of electrodes, the first fixation element being located between two electrodes of the plurality of electrodes.

12. The method of claim 9, wherein the medical elongated member comprises the lead and the longitudinally-extending section of the second outer surface portion extends from the distal end of the medical elongated member to a proximal side of the at least one electrode.

13. The method of claim 9, wherein the medical elongated member comprises the lead and the at least one electrode extends around less than one hundred percent of the outer perimeter of the medical elongated member.

14. The method of claim 1, wherein the medical elongated member is a paddle lead and the first outer surface portion is a first side of the paddle lead and the second outer surface portion is a second side of the paddle lead opposite the first side.

15. The method of claim 1, further comprising coupling the medical elongated member to a medical device, wherein the medical device is configured to deliver a therapy to the target tissue site via the medical elongated member or sense a physiological parameter of the patient via the medical elongated member.

16. The method of claim 15, wherein the medical device comprises at least one of a neurostimulator, fluid delivery device or sensor.

17. The method of claim 1, wherein the medical elongated member comprises an exposed adhesive fixation element along at least a part of the second outer surface portion.

18. The method of claim 1, wherein the first and second outer surface portions have substantially equal sizes.

19. The method of claim 1, wherein the first fixation element comprises at least one of a tine, a barb, a hook, an adhesive element, a flange, a balloon or a wire-like element.

20. The method of claim 1, wherein the first and second outer surface portions are adjacent to each other in a cross-sectional plane that extends through the elongated member at the axial position along the longitudinal axis of the elongated member.

21. The method of claim 20, wherein the first and second outer surface portions define an outer perimeter of the elongated member in the cross-sectional plane that extends through the elongated member at the axial position along the longitudinal axis of the elongated member.

22. The method of claim 1, wherein each of the first and second outer surface portions defines less than 100% of an outer perimeter of the elongated member.

23. The method of claim 1, wherein the second fixation element comprises at least one of a tine, a barb, a hook, a wire-like fixation element, an adhesive, a balloon-like fixation element, a pinning fixation element, a collapsible fixation structure, or an expandable fixation structure.

24. The method of claim 23, wherein the second fixation element comprises at a tine.

25. The method of claim 1, wherein the elongated member further comprises a third fixation element extending from the first outer surface portion and wherein, upon orientation of the second fixation element in a substantially superficial direction, the third fixation element extends from the outer surface in a superficial direction.

* * * * *